United States Patent [19]
Kodaka et al.

[11] Patent Number: 5,219,868
[45] Date of Patent: Jun. 15, 1993

[54] IMIDAZOLIDINE DERIVATIVES, PREPARATION THEREOF, INSECTICIDES CONTAINING SAME AS AN EFFECTIVE INGREDIENT AND INTERMEDIATES THEREFOR

[75] Inventors: Kenji Kodaka; Katsutoshi Kinoshita; Michihiko Nakaya; Koichi Ebihara; Shirou Shiraishi; Eiichi Yamada, all of Mobara; Satoshi Numata, Chiba, all of Japan

[73] Assignee: Mitsui Toatsu Chemicals, Inc., Tokyo, Japan

[21] Appl. No.: 802,092

[22] Filed: Dec. 4, 1991

[30] Foreign Application Priority Data

Dec. 10, 1990 [JP] Japan ................... 2-407153

[51] Int. Cl.$^5$ ................ A01N 43/50; C07D 401/12
[52] U.S. Cl. ................. 514/333; 514/341; 546/256; 546/278
[58] Field of Search ........... 546/278, 256; 514/333, 514/341

[56] References Cited

U.S. PATENT DOCUMENTS

| | | |
|---|---|---|
| 4,742,060 | 5/1988 | Shiokawa et al. |
| 4,845,106 | 7/1989 | Shiokawa et al. |
| 4,880,933 | 11/1989 | Shiokawa et al. |
| 4,914,113 | 4/1990 | Shiokawa et al. |
| 5,001,138 | 3/1991 | Shiokawa et al. |

FOREIGN PATENT DOCUMENTS

0455000A1 11/1991 European Pat. Off.

OTHER PUBLICATIONS

McKay et al, "Preparation and Properties of 2-Nitramino-$\Delta^2$-1,3-diazacycloalkenes", J. Am. Chem. Soc. 70, 430–432.

Roberts, R., "Acid Catalyzed Reaction of Diarylformamides with Ethyl Orthoformate", J. Am. Chem. Soc. 71, 3848–3849 (1949).

Roberts et al, "Orthoesters, Imidic esters and Amidines IV. The mechanism of the reaction of Aniline . . . " J. Am. Chem. Soc. 76, 2411–2414 (1954).

Tilley et al, "Synthesis of heterocyclic analogs of $\alpha$-methyldopa", J. Heterocyclic Chem., 16, 333–337 (1979).

Sullivan et al, "$\alpha$-Bromo- and $\alpha$-Cloropyridylalanines", J. Am. Med. Chem., 14, 557–558 (1971).

*The Chemistry of Amidines and Imidates*, vol. 2, Patai et al., Eds., John Wiley & Sons, New York, p. 343 (1991).

Lenoir, "The Application of Low–Valent Titanium Reagents in Organic Synthesis, " Synthesis, pp. 883–397 (Dec. 1989).

Primary Examiner—C. Warren Ivy
Assistant Examiner—P. G. Spivack
Attorney, Agent, or Firm—Millen, White, Zelano & Branigan

[57] ABSTRACT

Herein disclosed are novel imidazolidine derivatives of the formula (I) and intermediates of the formula (II)

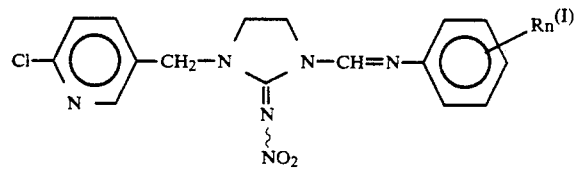

wherein each R represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl.group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3, (Abstract continued on next page.)

ABSTRACT
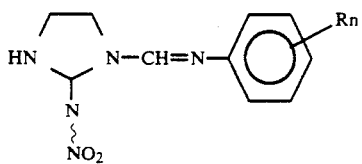
wherein R and n have, respectively, the same meanings as defined above. Processes for preparing the compounds of the formulas (I) and (II) are also described. Moreover, insecticidal compositions comprising an effective amount of the derivative (I) are described.
14 Claims, No Drawings

IMIDAZOLIDINE DERIVATIVES, PREPARATION THEREOF, INSECTICIDES CONTAINING SAME AS AN EFFECTIVE INGREDIENT AND INTERMEDIATES THEREFOR

BACKGROUND OF THE INVENTION

1. Field of the Invention

This invention relates to novel imidazolidine derivatives, their preparation, insecticides containing the derivatives as an effective ingredient and novel intermediates. More particularly, the invention relates to imidazolidine derivatives of the formula (I), a preparation process thereof, and insecticides containing the derivatives as an effective ingredient

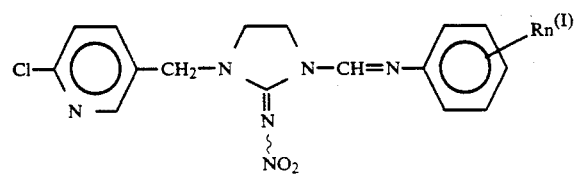

wherein the curved valance between the imine nitrogen atom and the nitro group means that Formula (I) is inclusive of both the E and the Z isomers and wherein each R represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3, and also to intermediate compounds of the formula (II) and a preparation process thereof

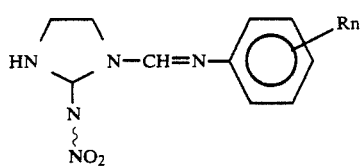

wherein R and n have, respectively, the same meanings as defined above.

The imidazolidine derivatives (I) of the invention are useful as an agricultural chemical (particularly, as an insecticide) in the fields of agriculture and the imidazolidine derivatives (II) are useful in various industrial fields and particularly as intermediates for agricultural chemicals.

2. Description of the Prior Art

A great number of insecticidal compounds having the imidazolidine derivative skeleton are known, for example, in Japanese Laid-open Patent Application Nos. 62-81382 and 63-156786, and the like.

There are also known a number of compounds having the imidazolidine skeleton, for example, in Japanese Laid-open Patent Application No. 63-156786 and the like.

SUMMARY OF THE INVENTION

It is an object of the present invention to provide novel imidazolidine derivatives having very good insecticidal activity and a simple process for preparing the derivatives.

It is another object of the invention to provide insecticides of high activity containing the derivatives as an effective ingredient.

It is a further object of the invention to provide novel intermediate compounds for the imidazolidine derivatives.

According to one embodiment of the invention, there is provided a novel imidazolidine derivative of the formula (I)

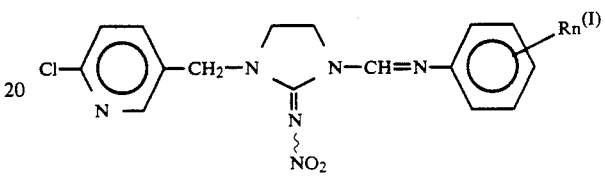

wherein each R represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3.

According to another embodiment of the invention, there is also provided a compound of the following general formula (II)

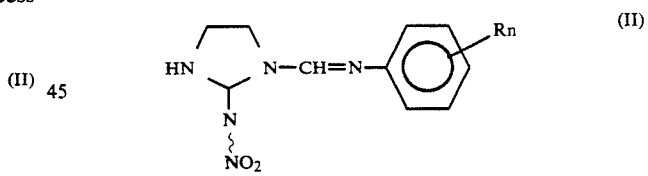

wherein each R represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3.

According to a further embodiment of the invention, there is provided a process for preparing the imidazolidine derivative of the formula (I) defined above by reaction between the compound of the general formula (II) defined above and a compound of the following general formula (III)

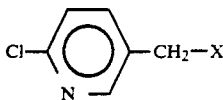

wherein X represents a chlorine atom or a bromine atom.

According to a still further embodiment of the invention, there is provided an insecticidal composition which comprises an effective amount of the compound of the general formula (I) defined above.

Moreover, the imidazolidine derivatives of the general formula (II) can be prepared by different processes. These processes are also within the scope of the invention.

According to one of the processes, there is provided a process for preparing an imidazolidine derivative of the general formula (II) which comprises reacting a compound of the following general formula (IV)

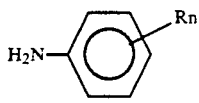

wherein each R has the same meaning as defined above and represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3, with a compound of the general formula (V)

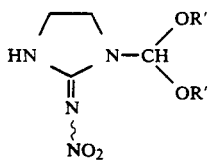

wherein each R' represents a lower alkyl group.

Another process for preparing an imidazolidine derivative of the general formula (II) defined before comprises reacting a compound of the following general formula (VI)

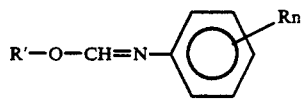

wherein each R has the same meaning as defined above and represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, R' represents a lower alkyl group, and n is an integer of from 1 to 3, with 2-nitroiminoimidazolidine of the following formula (VII)

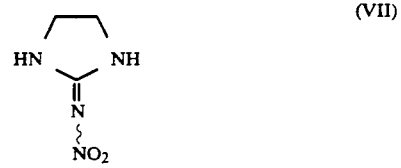

As will be apparent from the above, the invention is directed to novel imidazolidine derivatives of the formula (I), their preparation, insecticidal compositions comprising the derivative (I), novel intermediates of the formula (II) useful for preparing the derivative (I), and processes for preparing the intermediates (II).

DETAILED DESCRIPTION AND EMBODIMENTS OF THE INVENTION

In the formulas (I), (II), (IV) and (VI) set forth above, R's may be the same or different and each represents those groups or atoms defined before. Specific examples of R other than a methylenedioxy group, a hydroxy group, a cyano group, a nitro group and a benzyl group, include an alkyl group such as a methyl group, an ethyl group, a n-propyl group, an iso-propyl group, a n-butyl group, an iso-butyl group, a sec-butyl group, a tert-butyl group, a n-pentyl group, a n-hexyl group or the like; a halogen atom such as a fluorine atom, a chlorine atom, a bromine atom or an iodine atom; an alkoxy group such as a methoxy group, an ethoxy group, a n-propoxy group, an iso-propoxy group, a n-butoxy group, an iso-butoxy group, a sec-butoxy group, a n-pentyloxy group or the like; an alkylthio group such as a methylthio group, an ethylthio group, a n-propylthio group, an iso-propylthio group, a n-butylthio group or the like; a haloalkyl group such as a fuluoromethyl group, a chloromethyl group, a bromomethyl group, a trifuluoromethyl group, a trichloromethyl group, a tribromomethyl group, a 2-chloroethyl group, a 2-bromoethyl group, a 2,2,2-trifuluoroethyl group, a 3,3,3-trifuluoropropyl group or the like. a haloalkoxy group such as a difluoromethoxy group, a trifluoromethoxy group, a difluorochloromethoxy group, a difluorobromomethoxy group, a chloromethoxy group, a trifuluoromethyl group, a trichloromethyl group, a bromomethoxy group, a 2-chloroethoxy group, a 2-bromoethoxy group, a 1,1-difluoro-2,2-dichloroethoxy group, a 1,1-dibromo-2,2,2-trifluoroethoxy group, a 2,2-dichloroethoxy group, a 2,2,2-trichloroethoxy group, a 1,2-dichloroethoxy group, a 3-chloropropoxy group, a 3-bromopropoxy group, a 4-chlorobutoxy group, a 4-bromobutoxy group or the like; an alkylcarbonyl group such as an acetyl group, an ethylcarbonyl group, a n-propylcarbonyl group, an iso-propylcarbonyl group, a n-butylcarbonyl group, a sec-butylcarbonyl group, a tert-butylcarbonyl group, a n-propoxycarbonyl group, an iso-propoxycarbonyl group, a n-butoxycarbonyl group, a sec-butoxycarbonyl group, a tertbutoxycarbonyl group, a n-pentyloxycarbonyl group, a n-hexyloxycarbonyl group or the like; an alkylamino group such as a methylamino group, an ethylamino group, a propylamino group, an iso-propylamino group, a n-butylamino group, a sec-butylamino group, a tert-butylamino group, a dimethylamino group, a diethylamino group, a di-n-propylamino group, a di-iso-propylamino group, a di-n-butylamino group, a di-sec-butylamino group or the like; and a halopyridylmethyloxy group such as a 2-chloropyridine-6-ylmethyloxy group, a 2-chloropyridine-5-ylmethyloxy group, a 2-bromopyridine-6-ylmethyloxy group, a 2-bromopyridine-5-ylmethyloxy group or the like.

The compound of the formula (I) can be prepared according to the following reaction formula

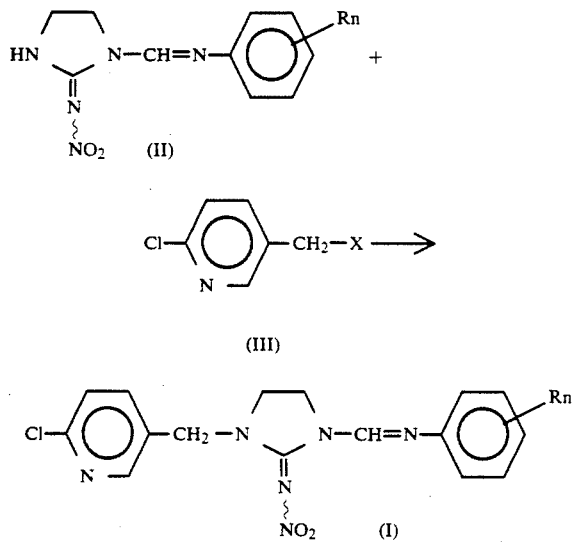

wherein R and n have, respectively, the same meanings as defined before and X represents a chlorine atom or a bromine atom.

More particularly, the 1-phenyliminomethyl-2-nitroiminoimidazolidine of the formula (II) and the chloropyridylmethyl halide of the formula (III) are reacted in the presence of a deacidifying agent in various solvents to readily prepare the compound of the formula (I).

Examples of the deacidifying agent include alkali metal hydroxides such as sodium hydroxide, potassium hydroxide and the like, alkaline earth metal hydroxides such as magnesium hydroxide, calcium hydroxide and the like, alkali metal hydrides such as sodium hydride, potassium hydride and the like, alkali metal alcoholates such as sodium methylate, sodium ethylate and the like, alkali metal oxides such as sodium oxide, carbonates such as sodium carbonate, potassium carbonate and the like, hydrogencarbonates such as sodium hydrogencarbonate, potassium hydrogencarbonate and the like, hydrogensulfates such as sodium hydrogensulfate, potassium hydrogensulfate and the like, phosphates such as trisodium phosphate, disodiumphosphate and the like, acetates such as sodium acetate, potassium acetate and the like, organic bases such as triethylamine, DBU, DIMAP and the like, butyl lithium, sodium amide, and the like. The solvents may include not only water, but also aromatic hydrocarbons such as benzene, toluene, xylene and the like, aliphatic hydrocarbons such as hexane, heptane, petroleum benzine and the like, aprotic polar solvents such as dimethylformamide, dimethylacetamide, dimethylsulfoxide, 1,3-dimethyl-2-imidazolidinone, 1-methyl-2-pyrrolidinone and the like, ethers such as ethyl ether, diisopropyl ether, 1,2-dimethoxyethane, tetrahydrofuran, dioxane and the like, nitriles such as acetonitrile, propionitrile and the like, and ketones such as acetone, diisopropyl ketone and the like. When there are used phase transfer catalysts such as tetrabutylammonium bromide, triethylbenzylammonium chloride and the like, intended imidazolidine derivatives (I) can be obtained in high yield.

The reaction temperature and the reaction time can be varied over wide ranges. In general, the reaction temperature is in the range of −20° to 200° C., preferably from 0° to 100° C. and the reaction time is in the range of from 0.01 to 30 hours, preferably from 0.1 to 15 hours.

It is not always necessary but is possible to react a protective group with a substituent group of the compound of the formula (II) to prepare a derivative of intended compound (I) and to remove the protective group from the derivative, thereby obtaining an imidazolidine derivative (I).

In the above reaction formula, the starting substance of the formula (II) can be prepared according to either process A or process B using the respective reaction sequences indicated below.

Process A:

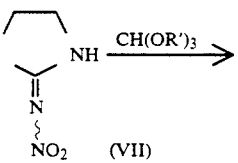

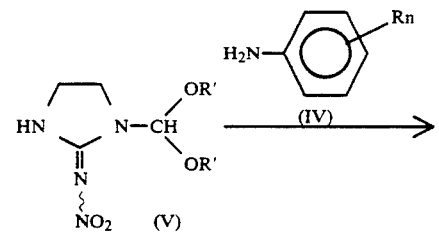

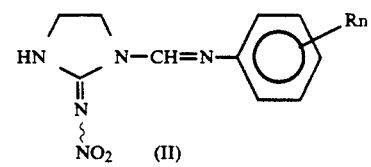

Process B

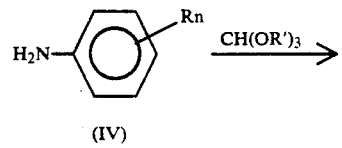

-continued
Process B

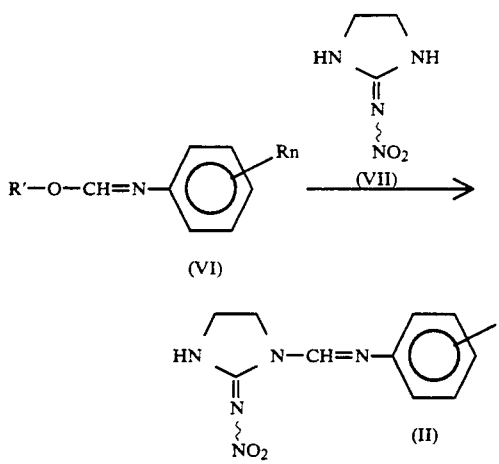

In process A, the compound (II) can be readily obtained in high yield by reaction between the 1-dialkoxymethyl-2-nitroiminoimidazolidine and the aniline derivative of the formula (IV). In the above reaction formula, the compound of the formula (V) can be prepared by reaction between 2-nitroiminoimidazolidine of the formula (VII) reported, for example, in J. Am. Chem. Soc., 70, 430 (1948), and a lower alkyl ester of orthoformic acid. This reaction can be performed in the absence of any solvent or in a solvent. Examples of the solvent include aprotic polar solvents such as dimethylformamide, dimethylsulfoxide, 1,3-dimethyl-2-imidazolidinone and the like.

The reaction temperature is in the range of from 50° to 200° C. and the reaction time is in the range of from 0.5 to 15 hours. The ratio by mole of the lower alkyl ester of orthoformic acid to the 2-nitroiminoimidazolidine (VII) is preferably in the range of 1-10.

The compound (V) contains a tautomer of the following formula

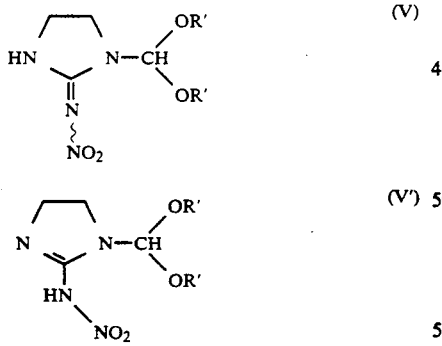

The compound of the formula (II) is a novel compound which has been prepared by us for the first time. The reaction sequence therefor is also a novel reaction which we have found first. This reaction can be performed in the absence of any solvent or in a solvent.

Examples of the solvent include aromatic hydrocarbons such as benzene, toluene, xylene and the like, aliphatic hydrocarbons such as hexane, heptane, petroleum benzine and the like, halogenated hydrocarbons such as chloroform, 1,2-dichloroethane and the like, aprotic polar solvents such as dimethylformamide, dimethylacetamide, dimethylsulfoxide, 1,3-dimethyl-2-imidazolidinone and the like, ethers such as ethyl ether, diisopropyl ether, 1,2-dimethoxyethane, tetrahydrofuran, dioxane and the like, nitriles such as acetonitrile, propionitrile and the like, and ketones such as acetone, diisopropyl ketone and the like. Although not necessarily required, catalysts may be used including mineral acids such as sulfuric acid, hydrochloric acid, phosphoric acid, nitric acid and the like, sulfonic acids such as p-toluenesulfonic acid, methanesulfonic acid, trifluoromethanesulfonic acid and the like, carboxylic acids such as acetic acid, benzoic acid, formic acid and the like, Lewis acids such as aluminium chloride, tin tetrachloride, zinc chloride, boron trifluoride, titanium tetrachloride and the like, pyridine hydrochloric acid salt, ammonium salts such as tetrabutylammonium chloride, and acidic or basic oxides such as zirconium oxide, silica gel, alumina and the like, acidic gases such as sulfur dioxide, carbon dioxide and the like, phenols and the like.

The reaction temperature and the reaction time may be varied widely. In general, the reaction temperature is in the range of from −80° C. to 300° C., preferably from −30° C. to 200° C.

The reaction is usually carried out under normal pressures but may be performed under pressure.

The reaction time is in the range of from 0.001 to 30 hours, preferably from 0.01 to 20 hours.

The amount of the aniline derivative (IV) may be not less than 1.0 mole per mole of the 1-dialkoxymethyl-2-nitroiminoimidazolidine (V) and is preferably in the range of from 0.3 to 10.0 moles in view of the economy.

The compound of the formula (II) can also be readily prepared in high yield by process B using the reaction between the phenyliminomethylalkyl ether derivative of the formula (VI) (reference: J.A.C.S., 71, 3848 (1949) and J.A.C.S., 76, 2411 (1954) and the 2-nitroiminoimidazolidine (VII). This reaction is also a novel reaction which we have found first. The reaction can be performed in the absence of or in solvent.

Examples of the solvent include aromatic hydrocarbons such as benzene, toluene, xylene and the like, aliphatic hydrocarbons such as hexane, heptane, petroleum benzine and the like, halogenated hydrocarbons such as chloroform, 1,2-dichloroethane and the like, aprotic polar solvents such as dimethylformamide, dimethylacetamide, dimethylsulfoxide, 1,3-dimethyl-2-imidazolidinone, 1-methyl-2-pyrrolidinone and the like, ethers such as ethyl ether, diisopropyl ether, 1,2-dimethoxyethane, tetrahydrofuran, dioxane and the like, nitriles such as acetonitrile, propionitrile and the like, and ketones such as acetone, diisopropyl ketone and the like.

Although not necessarily required, catalysts may be used including mineral acids such as sulfuric acid, hydrochloric acid, phosphoric acid, nitric acid and the like, sulfonic acids such as p-toluenesulfonic acid, methanesulfonic acid, trifluoromethanesulfonic acid and the like, carboxylic acids such as acetic acid, benzoic acid, formic acid and the like, Lewis acids such as aluminium chloride, tin tetrachloride, zinc chloride, boron trifluoride, titanium tetrachloride and the like, pyridine hydrochloric acid salt, ammonium salts such as tetrabutylammonium chloride, and acidic or basic oxides such as zirconium oxide, silica gel, alumina and the like, acidic gases such as sulfur dioxide, carbon dioxide and the like, phenols and the like.

The reaction temperature and the reaction time may be varied widely. In general, the reaction temperature is in the range of from −80° C. to 300° C., preferably from −30° C. to 200° C.

The reaction is usually carried out under normal pressures but may be performed under pressure.

The reaction time is in the range of from 0.001 to 30 hours, preferably from 0.01 to 20 hours.

The amount of the phenyliminomethyl ether derivative may be not less than 1.0 mole per mole of the 2-nitroiminoimidazolidine (VII) and is preferably in the range of from 1.0 to 10.0 moles in view of the economy.

In the above processes A and B, a one-pot reaction is effective wherein the aniline derivative (IV) or 2-nitroiminoimidazolidine (VII) is added without isolation of the compound (V) or (VI).

The compound (II) of the invention contains isomers of E and Z and a tautomer indicated below

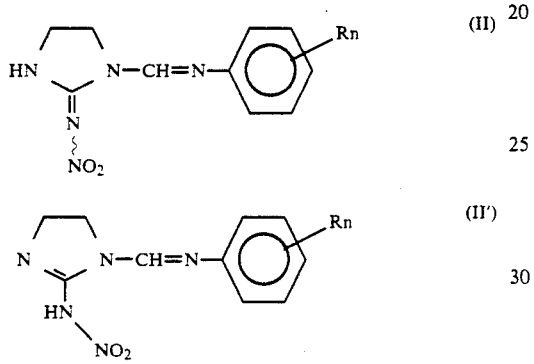

The compound (I) of the invention has two imine bonds and contains isomers E, Z.

On the other hand, chloropyridylmethyl halides of the formula (III) are known compounds and can be prepared according to a process described in literature (J. Heterocyclic Chem., 16, 333 (1979) and J. Med. Chem., 14, 557 (1971)).

The derivatives of the formula (I) according to the invention has great insecticidal activity and can be employed as an insecticide. The derivatives of the formula (I) of the invention show a good control effect against harmful insects without involving any phytotoxicity to cultivated plants.

Insect pests to which the derivatives of the invention can be applied include are set forth below.

Scientific Name-Common Name

1. Lepidoptera:
   *Pieris rapae crucivora* Boisduval—Common cabbageworm
   *Spodoptera litura* Fabricius—Common cutworm
   *Ostrinia furnacalis* Guenee—Oriental corn borer
   *Plutella xylostella* Linne—Diamond backmoth
   *Chilo supprossalis* Walker—Rice stem borer
   *Cnaphalocrocis medinalis* Guenee—Grass lead roller
2. Hemiptera:
   *Nephotettix cincticeps* Uhler—Green rice leafhopper
   *Nilaparvata lugens* Stal—Brown rice planthopper
   *Laodelphax striatellus* Fallen—Small brown planthopper
   *Unaspis yanonensis* Kuwana—Arrowhead scale
   *Myzus persicae* Sulzer—Green peach aphid
   *Aphis gossypii* Glover—Cotton aphid
   *Lipaphis pseudobrassicae* Davis—Turnip aphid
   *Nezara antennata* Scott—Common green stink bug
   *Trialeurodes vaporariorum* Westwood—Greenhouse whitefly
3. Coleoptera:
   *Callosobruchus chinensis* Linne—Azuki bean weevil
   *Sitophilus oryzae* Linne—Rice Weevil
   *Henosepilachna vigintioctopunctata* Fablicius—Spotted lady beetle
   *Anomala rufocuprea* Motschulsky—Soy bean beetle
   *Leptinotarsa decemlineata* Say—Colorado potato beetle
   *Echinocnemis squameus* Billberg—Rice plant weevil
4. Orthoptera:
   *Blattella germanica* Linne—German cockroach
   *Periplaneta americana* Linne—American cockroach
   *Gryllotalpa africana palisot* de Beauvois—African mole cricket
   *Locusta migratoria danica* Linne—Asiatic locust
   *Reticulitermes speratus kolbe*
   *Coptatermes formosanus* Shiraki—Formosan subleronean termite
   Diptera
   *Musca domestica vicina* Macuart—House fly
   *Aedes aegypti* Linne—Yellow fever mosquito
   *Culex pipiens pallens*—Coquillett
   *Culex tretaeniorhymus*—Giles Where the compounds of the formula (I) of the invention is actually applied, it may be used singly without addition of any other ingredient. However, it is usual to formulate carriers in order to make easy application as a control chemical.

For preparation of the compounds of the invention, any specific requirement is not necessary and arbitrary preparations, such as emulsions, wettable powders, dusts, granules, fine powders, oils, aerosols, poisonous feeds and the like, according to the procedures of preparing general agricultural chemicals well known in the art.

The term "carrier" used herein is intended to mean synthetic or natural, organic or inorganic materials which assist the effective ingredient to arrive at sites or portions to be treated and which are formulated in order to make easy storage, transport and handling of the effective compound.

Appropriate solid carriers include, for example, clays such as montomorillonite, kaolinite and the like, inorganic substances such as diatomaceous earth, white clay, talc, vermiculite, gypsum, calcium carbonate, silica gel, ammonium sulfate and the like, plant organic substances such as soybean flour, saw dust, wheat flour and the like, and urea.

Suitable liquid carriers include, for example, aromatic hydrocarbons such as toluene, xylene, cumene and the like, paraffin hydrocarbons such as kerosine, mineral oils and the like, ketones such as acetone, methyl ethyl ketone, cyclohexanone and the like, ethers such as dioxane, tetrahydrofuran and the like, glymes such as ethylene glycol dimethyl ether, ethylene glycol diethyl ether and the like, alcohols such as methanol, ethanol, propanol, ethylene glycol and the like, dimethylformamide, dimethyl sulfoxide, water and the like.

In order to reinforce the efficacy of the compound of the formula (I) of the invention, the following adjuvants may be used singly or in combination, depending on the type of preparation, the manner of application and the purpose.

For the purposes of emulsification, dispersion, spreading, wetting, bonding and stabilization, there are used water-soluble salts such as ligninsulfonates, nonionic surface active agents such as alkylbenzene sulfonates, alkylsulfates and the like, lubricants such as calcium stearate, waxes and the like, stabilizers such as isopropoxyhydrogenphosphates, and methyl cellulose, carboxymethyl cellulose, casein, gum arabi and the like. It should be noted that the adjuvants are not limited to those mentioned above.

The compounds of the formula (I) of the invention may develop better insecticidal activity when used in combination of two or more. If other physiologically active substances or chemicals are used in combination, multi-purpose compositions with good efficacy can be prepared with the possibility of developing a synergistic effect. Examples of such physiologically active substances include: synthetic pyrethroids, and isomers thereof or pyrethrum extracts, such as allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate and other known cyclopropanecarboxylic acid esters, 3-phenoxybenzyl 2,2-dimethyl-3-(2,2-dichlorovinyl)-cyclopropane-1-carboxylate, 3-phenoxy-α-cyanobenzyl 2,2-dimethyl-3-(2,2-dibromovinyl)-cyclopropane-1-carboxylate, 3-phenoxy-α-cyanobenzyl α-isopropyl-4-chlorophenylacetate and the like; organo-phosphate insecticides such as O,O-diethyl-O-(3-oxo-2-phenyl-2H-pyridazin-6-yl)-phosphorothioate (available from Mitsui-Toatsu Chem. Ind. Co., Ltd. under the trade name of Ofunack), O,O-dimethyl-O-(2,2-dichlorovinyl)phosphate (DDVP), O,O-dimethyl-O-(3-methyl-4-nitrophenyl)-phosphorothioate, diazinon, O,O-dimethyl-O-4-cyanophenylphosphorothioate, O,O-dimethyl-S-[α-(ethoxycarbonyl)benzyl]phosphorodithioate, 2-methoxy-4H-1,3,2-benzodioxaphosphorin-2-sulfide, O-ethyl-O-4-cyanophenylphosphonothioate and the like; carbamate insecticides such as 1-naphthyl N-methylcarbamate (NAC), m-tolyl N-methylcarbamate (MTMC), 2-dimethylamino-5,6-dimethylpyrimidin-4-yl dimethylcarbamate (Pyrimer), 3,4-dimethylphenyl N-methylcarbamate, 2-isopropoxyphenyl N-methylcarbamate and the like; aryl propyl ether insecticides such as 3-phenoxybenzyl 2-(4-chlorophenyl)-2-methyl propyl ether, 3-phenoxy-4-fluorobenzyl 2-(4-chlorophenyl)-2-methylpropyl ether, 3-phenoxybenzyl-2-(4-ethoxyphenyl)-2-methylpropyl ether, 3-phenoxy-4-fluorobenzyl-2-(4-ethoxyphenyl)-2-methylpropyl ether and the like; aromatic alkane insecticides such as 1-(3-phenoxyphenyl)-4-(4-chlorophenyl)-4-methylpentane, 1-(3-phenoxy 4-fluorophenyl)-4-(4-chlorophenyl)-4-methylpentane, 1-(3-phenoxyphenyl)-4-(4-ethoxyphenyl)-4-methylpentane, 1-(3-phenoxy-4-fluorophenyl)-4-(4-ethoxyphenyl)-4-methylpentane and the like; and other insecticides, acaricides, fungicides, nematicides, herbicides, plant growth regulators, fertilizes, BT agents, insect hormone compounds, and other pesticides.

Although the compounds of the formula (I) of the invention are stable against light, heat and oxidation, antioxidants or UV absorbers may be added in appropriate amounts, if necessary, including, for example, phenol derivatives or bisphenol derivatives such as BHT (2,6-di-t-butyl-4-methylphenol), BHA (butylhydroxyanisole) and the like, arylamines or benzophenone compounds such as phenyl-α-naphtylamine, phenyl-β-naphthylamine, a condensate of phenetidine and acetone, thereby obtaining more stable compositions.

When the compounds of the formula (I) of the invention are used as an insecticide, they are used in an amount of from 0.0001 to 95 wt %, preferably from 0.01 to 50 wt % of the insecticide.

When the insecticide of the invention is applied, the effective ingredient is used at a concentration of 0.01 to 5000 ppm, preferably from 0.1 to 1000 ppm.

The application amount per 10 area is generally in the range of from 1 to 300 of the effective ingredient.

The present invention is more particularly described by way of examples, which should not be construed as limiting the invention.

SYNTHESIS EXAMPLE 1

Compound No. 4

A mixture of 0.70 g of 1-(4-fluorophenyliminomethyl)-2-nitroiminoimidazolidine, 0.45 g of 2-chloro-5-chloromethylpyridine, 0.77 g of potassium carbonate and 5 ml of dimethylsulfoxide were agitated at 70° C. for 1 hour. The reaction mixture was, as it is, subjected to purification by column chromatography [silica gel, eluent: hexane-ethyl acetate (1:2)] to give 0.45 g of 1-(2-chloropyridin-5-ylmethyl)-2-nitroimino-3-(4-fluorophenyliminomethyl)imidazolidine.

SYNTHESIS EXAMPLE 2

Compound No. 14

A mixture of 4.00 g of 1-(4-ethylphenyliminomethyl)-2-nitroiminoimidazolidine, 3.00 g of 2-chloro-5-chloromethylpyridine, 4.20 g of potassium carbonate, and 10 ml of DMSO was agitated at 60° C. for 1 hour. The reaction mixture was poured into water, extracted with ethyl acetate, washed with water, dried and evaporated to give an oily residue, followed by purification with column chromatography [silica gel, eluent: hexane-ethyl acetate (1:2)] to obtain 2.70 g of 1-(2-chloropyridin-5-ylmethyl)-2-nitroimino-3-(4-ethylphenyliminomethyl)imidazolidine.

SYNTHESIS EXAMPLE 3

Compound No. 15

A mixture of 0.8 g of 1-(2-n-propylphenyliminomethyl)-nitroiminoimidazolidine, 0.42 g of 2-chloro-5-chloromethylpyridine, 0.36 g of potassium carbonate and 8 ml of acetonitrile were refluxed under heating conditions for 4 hours. The reaction mixture was evaporated and purified by column chromatography [silica gel, eluent: hexane-ethyl acetate (1:2)] to give 0.32 g of 1-(2-chloropyridin-5-ylmethyl)-2-nitroimino-3-(2-propylphenyliminomethyl)imidazolidine.

SYNTHESIS EXAMPLE 4

Compound No. 23

A mixture of 71,0 g of 1-(3,4-dimethylphenyliminomethyl)-2-nitroiminoimidazolidine, 48.5 g of 2-chloro-5-chloromethylpyridine, 50.0 g of potassium carbonate and 200 g of dimethylsulfoxide was agitated at 70° C. for 1 hour. After cooling to room temperature, about 800 ml of water and about 200 ml of ethyl acetate were added to the reaction mixture, followed by agitation, separation into settled crystals and a filtrate, washing with water, drying and recrystallization of a combination of the crystals with those obtained by concentration to about 1/5 from about 400 ml of acetonitrile to give 41 g of 1-(2-chloropyridine-5-ylmethyl)-2-nitroimino-3-(3,4-dimethylphenyliminomethyl)imidazolidine.

SYNTHESIS EXAMPLE 5

Compound No. 35

A mixture of 3.00 g of 1-(4-acetylphenyliminomethyl)-2-nitroiminoimidazolidine, 2.12 g of 2-chloro-5-chloromethylpyridine, 3.01 g of potassium carbonate, and 7 ml of DMSO was agitated at 60° C. for 1 hour. The reaction mixture was poured into water, extracted with ethyl acetate, washed with water, dried and evaporated to obtain an oily residue. To the resultant oily residue was added ethyl acetate, followed by separation of the resultant crystals by filtration and drying to give 1.73 g of 1-(2-chloropyridine-5-ylmethyl)-2-nitroimino-3-(4-acetylphenyliminomethyl)imidazolidine.

SYNTHESIS EXAMPLE 6

Compound No. 36

A mixture of 3.74 g of 1-(4-N,N-dimethylaminophenyliminomethyl)-2-nitroiminoimidazolidine, 2.65 9 of 2-chloro-5-chloromethylpyridine, 3.75 g of potassium carbonate, and 10 ml of DMSO was agitated at 60° C. for 1 hour. The reaction mixture was poured into water, extracted with ethyl acetate, washed with water, dried and evaporated to give an oily residue. To the resultant oily residue was added ethyl acetate, followed by separation of the resultant crystals by filtration and drying to give 2.80 g of 1-(2-chloropyridin-5-ylmethyl)-2-nitroimino-3-(4-N,N-dimethylaminophenyliminomethyl)imidazolidine.

SYNTHESIS EXAMPLE 7

Compound No. 37

A mixture of 1.00 g of 1-(4-ethoxyoarbonylphenyliminomethyl)-2-nitroiminoimidazolidine, 10 ml of dimethylsulfoxide, 0.58 g of sodium hydrogencarbonate, and 0.67 g of 2-chloro-5-chloromethylpyridine was agitated at 60° C. for 3 hours. The reaction mixture was poured into a saline solution, extracted with ethyl acetate, dried over anhydrous sodium sulfate and evaporated, followed by purification with column chromatography [silica gel, eluent: ethyl acetate] to give 1.25 g of 1-(2-chloropyridin-5-ylmethyl)-2-nitroimino-3-(4-ethoxycarbonylphenylimionomethyl)imidazolidine.

SYNTHESIS EXAMPLE 8

Compound No. 37

A mixture of 1.0 g of 1-(4-ethoxycarbonylphenyliminomethyl)-2-nitroiminoimidazolidine, 10 ml of dimethylsulfoxide and 0.14 g of sodium hydride was agitated at 60° C. for 30 minutes, to which 0.67 g of 2-chloro-5-chloromethylpyridine was added and agitated 80° C. for 1 hour. The reaction mixture was poured into a saline solution, extracted with ethyl acetate, dried over anhydrous sodium sulfate and evaporated, followed by purification with column chromatography [silica gel, eluent: ethyl acetate] to give 1.25 g of 1-(2-chloropyridin-5-ylmethyl)-2-nitroimino-3-(4-ethoxy-carbonylphenylimionomethyl)imidazolidine.

SYNTHESIS EXAMPLE 9

Compound No. 47

A mixture of 46.0 g of 1-(2-methylmercaptophenyliminomethyl)-2-nitroiminoimidazolidine, 32.0 g of 2-chloro-5-chloromethylpyridine, 45.6 g of potassium carbonate and 350 ml of dimethylsulfoxide was agitated at 65° to 70° C. for 1 hour. The reaction mixture was poured into about 200 ml of water, to which about 200 ml of ethyl acetate was added. The resultant crystals were collected by filtration, followed by sludging with hexane, washing with water and drying to give 31 g of 1-(2-chloropyridin-5-ylmethyl)-2-nitroimino-3-(2-methylmercaptophenyliminomethyl)imidazolidine.

Typical compounds of the formula (I) which could be prepared in the same manner as in Synthesis Examples 1 to 9 are shown in Table 1 along with those compounds of the above examples.

TABLE 1

$$Cl-\underset{N}{\underbrace{\bigcirc}}-CH_2-N\underset{\underset{NO_2}{\overset{\|}{N}}}{\overset{\frown}{\bigg\langle}}N-CH=N-\bigcirc-R_n$$

| Compound No. | $R_n$ | Values of Physical Properties |
|---|---|---|
| 1 | —H | $\delta_{TMS}$(CDCl$_3$)(ppm): 4.03~4.11(2H, m), 4.19~4.23(2H, m), 4.75(2H, s), 6.98~7.52(5H, m), 7.49(1H, d, J=8.1Hz), 7.92(1H, dd, J=8.1Hz, J=2.2Hz), 8.14(1H, d, J=2.2Hz), 8.49(1H, s) |
| 2 | 2-F | $\delta_{TMS}$(CDCl$_3$)(ppm): 4.01~4.09(2H, m), 4.25~4.30(2H, m), 4.75(2H, s), 7.09~7.20(4H, m), 7.49(1H, d, J=8.1Hz), 7.94(1H, dd, J=8.1Hz, J=2.2Hz), 8.26(1H, s), 8.50(1H, d, J=2.2Hz) |
| 3 | 3-F | $\delta_{TMS}$(acetone-d$_6$)(ppm): 4.01~4.08(2H, m), 4.24~4.28(2H, m), 4.75(2H, s), 6.81~6.91(3H, m), 7.30~7.36(1H, m), 7.49(1H, d, J=8.1Hz), 7.93(1H, dd, J=8.1Hz, J=2.2Hz), 8.21(1H, s), 8.49(1H, d, J=2.2Hz) |
| 4 | 4-F | $\delta_{TMS}$(CDCl$_3$)(ppm): 3.70~3.80(2H, m), 4.11~4.23(2H, m), 4.60(2H, s), 6.99~7.07(4H, m), 7.40(1H, d, J=8.1Hz), 7.74(1H, dd, J=8.1Hz, J=2.2Hz), 8.37(1H, d, J=2.2Hz), 8.18(1H, s) |
| 5 | 2,6-F$_2$ | $\delta_{TMS}$(acetone-d$_6$)(ppm): 4.04~4.09(2H, m), 4.26~4.30(2H, m), 4.75(2H, s), 6.99~7.16(3H, m), 7.50(1H, d, J=8.1Hz), 7.95(1H, dd, J=8.1Hz, J=2.2Hz), 8.42(1H, s), 8.51(1H, d, J=2.2Hz) |
| 6 | 3-Cl | $\delta_{TMS}$(acetone-d$_6$)(ppm): 4.00~4.06(2H, m), 4.24~4.28(2H, m), 4.75(2H, s), 7.00~7.39(4H, m), 7.48(1H, d, J=8.1Hz), 7.92(1H, dd, J=8.1Hz, J=2.2Hz), 8.21(1H, s), 8.48(1H, d, J=2.2Hz) |
| 7 | 4-Cl | $\delta_{TMS}$(CDCl$_3$)(ppm): 4.08~4.16(2H, m), 4.24~4.28(2H, m), 4.75(2H, s), 7.06~7.37(4H, m), 7.48(1H, d, J=8.1Hz), 7.92(1H, dd, J=8.1Hz, J=2.2Hz), 8.45(1H, s), 8.48(1H, d, J=2.2Hz) |
| 8 | 3-Br | $\delta_{TMS}$(CDCl$_3$)(ppm): 3.71~3.75(2H, m), 4.17~4.22(2H, m), 4.59(2H, s), 6.90~6.97(2H, m), 7.33~7.44(3H, m), 7.65~7.72(1H, m), 8.33(1H, d, J=2.2Hz), 8.36(1H, s) |
| 9 | 2-CH$_3$ | $\delta_{TMS}$(CDCl$_3$)(ppm): 2.12(3H, s), 3.87~3.91(2H, m), 4.15~4.20(2H, m), 4.62(2H, s), 6.93~7.38(4H, m), 7.37(1H, d, J=8.1Hz), 7.80(1H, dd, J=8.1Hz, J=2.2Hz), 7.91(1H, s), |

TABLE 1-continued

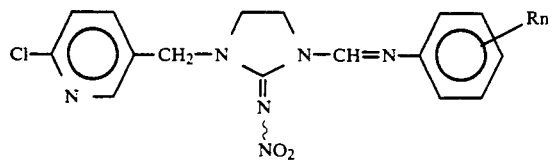

| Compound No. | $R_n$ | Values of Physical Properties |
|---|---|---|
| 10 | 3-CH$_3$ | $\delta_{TMS}$(CDCl$_3$)(ppm): 2.08(3H, s), 4.01~4.06(2H, m), 4.23~4.28(2H, m), 4.75(2H, s), 6.83~7.23(4H, m), 7.49(1H, d, J=8.1Hz), 7.93(1H, dd, J=8.1Hz, J=2.2Hz), 8.43(1H, s), 8.49(1H, d, J=2.2Hz) |
| 11 | 4-CH$_3$ | $\delta_{TMS}$(CDCl$_3$)(ppm): 2.30(3H, s), 3.93~4.04(2H, m), 4.23~4.27(2H, m), 4.74(2H, s), 6.87~7.21(4H, m), 7.49(1H, d, J=8.1Hz), 7.92(1H, dd, J=8.1Hz, J=2.2Hz), 8.44(1H, s), 8.48(1H, d, J=2.2Hz) |
| 12 | 2-Et | $\delta_{TMS}$(CDCl$_3$)(ppm): 1.15(3H, t, J=7.33Hz), 2.65(2H, q, J=7.33Hz), 3.70~3.75(2H, m), 4.22~4.26(2H, m), 4.61(2H, s), 6.81~6.84(1H, m), 7.11~7.21(3H, m), 7.40(1H, d, J=8.1Hz), 7.75(1H, dd, J=8.1Hz, J=2.2Hz), 8.13(1H, s), 8.38(1H, d, J=2.2Hz) m.p.: 115.0~118.0° C. |
| 13 | 3-Et | $\delta_{TMS}$(acetone-d$_6$)(ppm): 1.16~1.24(3H, t), 2.58~2.66(2H, q), 3.99~4.24(4H, m), 4.75(2H, s), 6.88~7.35(4H, m), 7.50(1H, d, J=8.1Hz), 7.93(1H, dd, J=8.1Hz, J=2.2Hz), 8.15(1H, s), 8.49(1H, d, J=2.2Hz) |
| 14 | 4-Et | $\delta_{TMS}$(acetone-d$_6$)(ppm): 1.96~2.06(3H, t), 2.56~2.64(2H, q), 3.82~4.08(2H, m), 4.22~4.27(2H, m), 4.74(2H, s), 6.96~7.23(4H, m), 7.48(1H, d, J=8.1Hz), 7.92(1H, dd, J=8.1Hz, J=2.2Hz), 8.14(1H, s), 8.48(1H, d, J=2.2Hz) |
| 15 | 2-nPr | $\delta_{TMS}$(acetone-d$_6$)(ppm): 0.89(3H, t, J=7.33Hz), 1.52~1.61(2H, m), 2.65(2H, t, J=7.33Hz), 3.99~4.08(2H, m), 4.28~4.33(2H, m), 4.75(2H, s), 6.89(1H, d, J=8.1Hz), 7.07~7.19(3H, m), 7.50(1H, d, J=8.1Hz), 7.93(1H, dd, J=8.1Hz, J=2.2Hz), 8.07(1H, s), 8.49(1H, d, J=2.2Hz) |
| 16 | 4-nPr | $\delta_{TMS}$(acetone-d$_6$)(ppm): 0.92(3H, t, J=7.30Hz), 1.57~1.66(2H, m), 2.57(2H, t, J=7.30Hz), 3.98~4.02(2H, m), 4.23~4.56(2H, m), 4.74(2H, s), 7.00(2H, d, J$_{AB}$=8.1Hz), 7.17(2H, d, J$_{AB}$=8.1Hz), 7.49(1H, d, J=8.1Hz), 7.93(1H, dd, J=8.1Hz, J=2.2Hz), 8.15(1H, s), 8.49(1H, d, J=2.2Hz) m.p.: 148.0~149.5° C. |
| 17 | 2-iPr | $\delta_{TMS}$(CDCl$_3$)(ppm): 1.19(6H, d, J=7.33Hz), 3.70~3.75(2H, m), 4.22~4.27(2H, m), 4.61(2H, s), 6.80~6.82(1H, m), 7.14~7.17(2H, m), 7.25~7.27(1H, m), 7.40(1H, d, J=8.1Hz), 7.76(1H, dd, J=8.1Hz, J=2.2Hz), 8.12(1H, s), 8.38(1H, d, J=2.2Hz) m.p.: 168.0~171.0° C. |
| 18 | 4-iPr | $\delta_{TMS}$(acetone-d$_6$)(ppm): 1.22(6H, d, J=7.30Hz), 2.84~2.93(1H, m), 3.97~4.08(2H, m), 4.23~4.28(2H, m), 4.74(2H, s), 6.99~7.35(4H, m), 7.49(1H, d, J=8.1Hz), 7.93(1H, dd, J=8.1Hz, J=2.2Hz), 8.15(1H, s), |

TABLE 1-continued

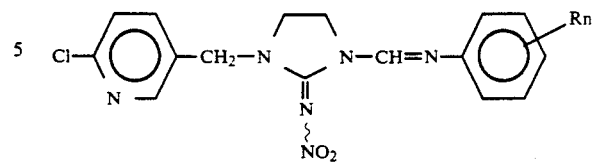

| Compound No. | $R_n$ | Values of Physical Properties |
|---|---|---|
|  |  | 8.49(1H, d, J=2.2Hz) m.p.: 94.0~101.0° C. |
| 19 | 2,3-(CH$_3$)$_2$ | $\delta_{TMS}$(CDCl$_3$)(ppm): 2.17(3H, s), 2.27(3H, s), 3.70~3.74(2H, m), 4.20~4.27(2H, m), 4.60(2H, s), 6.67~7.06(3H, m), 7.40(1H, d, J=8.1Hz), 7.75(1H, dd, J=8.1Hz, J=2.2Hz), 8.09(1H, s), 8.38(1H, d, J=2.2Hz) m.p.: 148.0~153.5° C. |
| 20 | 2,4-(CH$_3$)$_2$ | $\delta_{TMS}$(CDCl$_3$)(ppm): 2.21(3H, s), 2.29(3H, s), 3.69~3.73(2H, m), 4.21~4.25(2H, m), 4.60(2H, s), 6.73~7.02(3H, m), 7.39(1H, d, J=8.1Hz), 7.74(1H, dd, J=8.1Hz, J=2.2Hz), 8.10(1H, s), 8.37(1H, d, J=2.2Hz) |
| 21 | 2,5-(CH$_3$)$_2$ | $\delta_{TMS}$(CDCl$_3$)(ppm): 2.19(3H, s), 2.30(3H, s), 3.69~3.74(2H, m), 4.21~4.25(2H, m), 4.60(2H, s), 6.64(1H, s), 6.90(1H, d, J=7.3Hz), 7.05(1H, d, J=8.1Hz), 7.40(1H, d, J=8.1Hz), 7.75(1H, dd, J=8.1Hz, J=2.9Hz), 8.11(1H, s), 8.37(1H, d, J=2.2Hz) m.p.: 131.5~132.3° C. (dec.) |
| 22 | 2,6-(CH$_3$)$_2$ | $\delta_{TMS}$(CDCl$_3$)(ppm): 2.11(6H, s), 3.70~3.76(2H, m), 4.23~4.47(2H, m), 4.61(2H, s), 6.91~7.05(3H, m), 7.40(1H, d, J=8.1Hz), 7.75(1H, dd, J=8.1Hz, J=2.2Hz), 7.94(1H, s), 8.38(1H, d, J=2.2Hz) m.p.: 148.0~156.5° C. (dec.) |
| 23 | 3,4-(CH$_3$)$_2$ | $\delta_{TMS}$(CDCl$_3$)(ppm): 2.24(3H, s), 2.25(3H, s), 3.68~3.73(2H, m), 4.19~4.24(2H, m), 4.60(2H, s), 6.78~6.84(2H, m), 7.08(1H, d, J=8.1Hz), 7.40(1H, d, J=8.1Hz), 7.74(1H, dd, J=8.1Hz, J=2.2Hz), 8.20(1H, s), 8.37(1H, d, J=2.2Hz) m.p.: 142.4~142.6° C. (dec.) |
| 24 | 3,5-(CH$_3$)$_2$ | $\delta_{TMS}$(CDCl$_3$)(ppm): 2.30(6H, s), 3.68~3.73(2H, m), 4.18~4.23(2H, m), 4.60(2H, s), 6.66(2H, s), 6.83(1H, s), 7.40(1H, d, J=8.1Hz), 7.75(1H, dd, J=8.1Hz, J=2.9Hz), 8.20(1H, s), 8.37(1H, d, J=2.9Hz) m.p.: 127.9~130.5° C. (dec.) |
| 25 | 3-OCH$_3$ | $\delta_{TMS}$(CDCl$_3$)(ppm): 3.68~3.79((2H, m), 3.81(3H, s), 4.17~4.23(2H, m), 4.60(2H, s), 6.58~6.76(3H, m), 7.06~7.30(1H, m), 7.40(1H, d, J=8.1Hz), 7.74(1H, dd, J=8.1Hz, J=2.2Hz), 8.18(1H, s), 8.37(1H, d, J=2.2Hz) |
| 26 | 4-OCH$_3$ | $\delta_{TMS}$(CDCl$_3$)(ppm): 3.81(3H, s), 3.90~4.02(2H, m), 4.16~4.20(2H, m), 4.48(2H, s), 6.84~7.06(4H, m), 7.36(1H, d, J=8.1Hz), 7.74(1H, dd, J=8.1Hz, J=2.2Hz), 8.37(1H, d, J=2.2Hz), 8.39(1H, s) |
| 27 | 2-OEt | $\delta_{TMS}$(CDCl$_3$)(ppm): 1.41~1.48(3H, m), 4.04~4.09(2H, m), 4.10~4.14(2H, m), 4.24~4.29(2H, m), 4.60(2H, s), 7.03~7.13(3H, m), 7.34~7.43(1H, m), 7.39(1H, d, J=8.1Hz), 7.75(1H, dd, J=8.1Hz, J=2.2Hz), 8.39(1H, d, J=2.2Hz), 8.35(1H, s) |
| 28 | 4-OEt | $\delta_{TMS}$(CDCl$_3$)(ppm): 1.33~1.37(3H, |

TABLE 1-continued

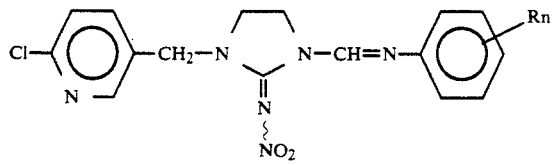

| Compound No. | $R_n$ | Values of Physical Properties |
|---|---|---|
| | | m), 3.96~4.08(4H, m), 4.22~4.26(2H, m), 4.73(2H, s), 6.87~6.91(2H, m), 7.03~7.06(2H, m), 7.45(1H, d, J=8.1Hz), 7.92(1H, dd, J=8.1Hz, J=2.2Hz), 8.15(1H, s), 8.48(1H, d, J=2.2Hz) |
| 29 | 2-OiPr | $\delta_{TMS}$(acetone-d$_6$)(ppm): 1.29(6H, d, J=6.60Hz), 3.97~4.02(2H, m), 4.24~4.29(2H, m), 4.58~4.70(1H, m), 4.74(2H, s), 6.88~7.10(4H, m), 7.49(1H, d, J=8.1Hz), 7.93(1H, dd, J=8.1Hz, J=2.2Hz), 8.49(1H, d, J=2.2Hz), 8.50(1H, s) |
| 30 | 3-OiPr | $\delta_{TMS}$(acetone-d$_6$)(ppm): 1.29(6H, d, J=4.9Hz), 3.98~4.03(2H, m), 4.23~4.27(2H, m), 4.56~4.65(1H, m), 4.74(2H, s), 6.61~6.66(2H, m), 6.66~6.71(1H, m), 7.19~7.35(1H, m), 7.50(1H, d, J=8.1Hz), 7.93(1H, dd, J=8.1Hz, J=2.2Hz), 8.14(1H, s), 8.49(1H, d, J=2.2Hz) |
| 31 | 4-OiPr | $\delta_{TMS}$(acetone-d$_6$)(ppm): 1.28(6H, d, J=5.9Hz), 3.97~4.01(2H, m), 4.22~4.27(2H, m), 4.55~4.61(1H, m), 4.74(2H, s), 6.89(2H, dd, $J_{AB}$=6.6Hz, $J_{AB}$=2.2Hz), 7.04(2H, dd, $J_{AB}$=6.6Hz, $J_{AB}$=2.2Hz), 7.49(1H, d, J=8.1Hz), 7.93(1H, dd, J=8.1Hz, J=2.2Hz), 8.15(1H, s), 8.49(1H, d, J=2.2Hz) m.p.: 125.5~127.3° C. |
| 32 | 3,4-Methylenedioxy | $\delta_{TMS}$(acetone-d$_6$)(ppm): 3.99~4.08(2H, m), 4.21~4.26(2H, m), 4.82(2H, s), 5.99(2H, s), 6.58(1H, dd, J=8.1Hz, J=2.2Hz), 6.68(1H, d, J=2.2Hz), 6.81(1H, d, J=8.1Hz), 6.99~7.35(4H, m), 7.49(1H, d, J=8.1Hz), 7.931(1H, dd, J=8.1Hz, J=2.2Hz), 8.15(1H, s), 8.48(1H, d, J=2.2Hz) m.p.: 84.0~88.0° C. |
| 33 | 2-COCH$_3$ | $\delta_{TMS}$(acetone-d$_6$)(ppm): 2.81(3H, s), 4.00~4.08(2H, m), 4.32~4.36(2H, m), 4.76(2H, s), 7.02~7.63(4H, m), 7.50(1H, d, J=8.1Hz), 7.93(1H, dd, J=8.1Hz, J=2.2Hz), 8.40(1H, s), 8.49(1H, d, J=2.2Hz) |
| 34 | 3-COCH$_3$ | $\delta_{TMS}$(acetone-d$_6$)(ppm): 2.58(3H, s), 4.00~4.07(2H, m), 4.26~4.30(2H, m), 4.75(2H, s), 7.28~7.81(4H, m), 7.48(1H, d, J=8.1Hz), 7.92(1H, dd, J=8.1Hz, J=2.2Hz), 8.24(1H, s), 8.48(1H, d, J=2.2Hz) |
| 35 | 4-COCH$_3$ | $\delta_{TMS}$(acetone-d$_6$)(ppm): 2.56(3H, s), 3.61~4.30(4H, m), 4.76(2H, s), 7.13~7.99(4H, m), 7.49(1H, d, J=8.1Hz), 7.99(1H, dd, J=8.1Hz, J=2.2Hz), 8.22(1H, s), 8.49(1H, d, J=2.2Hz) |
| 36 | 4-N(CH$_3$)$_2$ | $\delta_{TMS}$(CDCl$_3$)(ppm): 2.96(6H, s), 3.66~3.73(2H, m), 4.13~4.24(2H, m), 4.59(2H, s), 6.67~7.11(4H, m), 7.39(1H, d, J=8.1Hz), 7.75(1H, dd, J=8.1Hz, J=2.2Hz), 8.22(1H, s), 8.36(1H, d, J=2.2Hz) |
| 37 | 4-COOEt | $\delta_{TMS}$(acetone-d$_6$)(ppm): 1.33~1.41(3H, m), 3.90~4.08(2H, m), 4.26~4.35(4H, m), 4.79(2H, s), 7.13~7.20(2H, m), 7.45(2H, d, J=8.1Hz), 7.91~8.02(3H, m), 8.37(1H, |

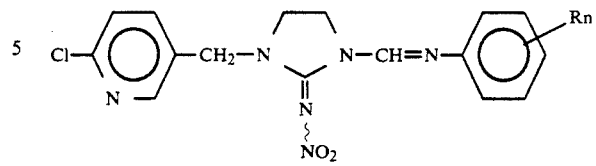

| Compound No. | $R_n$ | Values of Physical Properties |
|---|---|---|
| | | s), 8.41(1H, d, J=2.2Hz) |
| 38 | 2-CF$_3$ | $\delta_{TMS}$(CDCl$_3$)(ppm): 3.71~3.79(2H, m), 4.21~4.26(2H, m), 4.62(2H, s), 6.99(1H, d, J=8.1Hz), 7.35~7.77(5H, m), 8.15(1H, s), 8.38(1H, d, J=2.2Hz) m.p.: 160.1~163.1° C. (dec.) |
| 39 | 3-CF$_3$ | $\delta_{TMS}$(CDCl$_3$)(ppm): 3.72~3.77(2H, m), 4.19~4.24(2H, m), 4.61(2H, s), 7.19~7.46(5H, m), 7.74(1H, dd, J=8.4Hz, J=2.2Hz), 8.24(1H, s), 8.38(1H, d, J=2.9Hz) m.p.: 161.0~162.0° C. (dec.) |
| 40 | 4-CF$_3$ | $\delta_{TMS}$(CDCl$_3$)(ppm): 3.73~3.77(2H, m), 4.20~4.22(2H, m), 4.61(2H, s), 7.11~7.67(6H, m), 8.21(1H, s), 8.38(1H, d, J=2.9Hz) |
| 41 | 2-OCF$_3$ | $\delta_{TMS}$(CDCl$_3$)(ppm): 3.72~3.76(2H, m), 4.21~4.29(2H, m), 4.61(2H, s), 7.01~7.41(5H, m), 7.75(1H, dd, J=8.1Hz, J=2.9Hz), 8.20(1H, s), 8.38(1H, d, J=2.2Hz) |
| 42 | 4-OCF$_3$ | $\delta_{TMS}$(CDCl$_3$)(ppm): 3.71~3.75(2H, m), 4.19~4.23(2H, m), 4.61(2H, s), 7.04(2H, d, J=8.8Hz), 7.18(2H, d, J=8.8H), 7.39(1H, d, J=8.8Hz), 7.74(1H, dd, J=8.8Hz, 2.9Hz), 8.19(1H, s), 8.37(1H, d, J=2.9Hz) m.p.: 78.8~81.5° C. (dec.) |
| 43 | 3-OCF$_2$H | $\delta_{TMS}$(CDCl$_3$)(ppm): 3.71~3.75(2H, m), 4.18~4.23(2H, m), 4.60(2H, s), 6.51(1H, t, J=74.1Hz), 6.81~6.95(3H, m), 7.27~7.41(2H, m), 7.74(1H, dd, J=8.4Hz, J=2.2Hz), 8.20(1H, s), 8.37(1H, d, J=2.2Hz) |
| 44 | 2-NO$_2$ | $\delta_{TMS}$(CDCl$_3$)(ppm): 3.73~3.77(2H, m), 4.20~4.25(2H, m), 4.63(2H, s), 7.00~7.03(1H, m), 7.25~7.29(1H, m), 7.41(1H, d, J=8.8Hz), 7.54~7.58(1H, m), 7.75(1H, dd, J=8.8Hz, J=2.9Hz), 7.87~7.91(1H, m), 8.17(1H, s), 8.38(1H, d, J=2.9Hz) m.p.: 159.9~160.5° C. (dec.) |
| 45 | 3-NO$_2$ | $\delta_{TMS}$(CDCl$_3$)(ppm): 3.77~3.81(2H, m), 4.21~4.25(2H, m), 4.63(2H, s), 7.35~7.52(3H, m), 7.75(1H, dd, J=8.1Hz, J=2.2Hz), 7.88~8.05(2H, m), 8.39(1H, d, J=2.2Hz), 8.59(1H, s) |
| 46 | 2-CN | $\delta_{TMS}$(CDCl$_3$)(ppm): 3.74~3.78(2H, m), 4.26~4.32(2H, m), 4.52(2H, s), 7.07~7.76(6H, m), 8.27(1H, s), 8.38(1H, d, J=2.2Hz) |
| 47 | 2-SCH$_3$ | $\delta_{TMS}$(CDCl$_3$)(ppm): 3.70~3.74(2H, m), 4.25~4.30(2H, m), 4.60(2H, s), 6.87(1H, m), 7.09~7.21(3H, m), 7.39(1H, dd, J=8.1Hz), 7.75(1H, dd, J=8.1Hz, J=2.2Hz), 8.17(1H, s), 8.36(1H, d, J=2.2Hz) m.p.: 162.1~163.3° C. (dec.) |
| 48 | 2-Ph | $\delta_{TMS}$(CDCl$_3$)(ppm): 3.60~3.64(2H, m), 3.99~4.04(2H, m), 4.57(2H, s), 6.96(1H, dd, J=7.3Hz, J=1.5Hz), 7.28~7.44(9H, m), 7.73(1H, dd, J=8.1Hz, J=2.2Hz), 8.15(1H, s), 8.34(1H, d, J=2.9Hz) m.p.: 102.2~111.6° C. (dec.) |
| 49 | 4-OPh | $\delta_{TMS}$(CDCl$_3$)(ppm): 3.70~3.75(2H, m), 4.19~4.24(2H, m), 4.60(2H, s), |

TABLE 1-continued

[Structure: Cl-pyridyl-CH₂-N(imidazolidine ring with =N-NO₂)-N-CH=N-phenyl-Rn]

| Compound No. | Rₙ | Values of Physical Properties |
|---|---|---|
| | | 6.96~7.40(10H, m), 7.74(1H, dd, J=8.1Hz, 2.2Hz), 8.20(1H, s), 8.37(1H, d, J=2.2Hz) |
| 50 | 2-CH₂Ph | $\delta_{TMS}$(CDCl₃)(ppm): 3.63~3.68(2H, m), 4.09~4.14(2H, m), 4.58(2H, s), 6.89(1H, d, J=7.3Hz), 7.09~7.25(8H, m), 7.40(1H, d, J=8.1Hz), 7.73(1H, dd, J=8.1Hz, J=2.2Hz), 8.06(1H, s), 8.36(1H, d, J=2.2Hz) |
| | | m.p.: 152.6~154.8° C. (dec.) |
| 51 | 4-(2-chloro-pyridyl-methyloxy) | $\delta_{TMS}$(DMSO-d₆)(ppm): 3.79~3.85(2H, m), 4.09~4.13(2H, m), 4.65(2H, s), 5.13(2H, s), 6.99~7.07(4H, m), 7.53(1H, d, J=8.1Hz), 7.56(1H, d, J=8.1Hz), 7.87(1H, dd, J=8.1Hz, J=2.2Hz), 7.93(1H, d, J=8.1Hz, J=2.2Hz), 8.06(1H, s), 8.42(1H, d, J=2.2Hz), 8.50(1H, d, J=2.2Hz) |
| | | m.p.: 115.0~123.0° C. |
| 52 | 4-nBu | $\delta_{TMS}$(acetone-d₆)(ppm): 0.90(3H, t, J=7.34Hz), 1.30~1.38(2H, m), 1.54~1.60(2H, m), 2.57~2.62(2H, m), 3.97~4.02(2H, m), 4.22~4.27(2H, m), 4.73(2H, s), 6.99(2H, d, $J_{AB}$=8.1Hz), 7.16(2H, d, $J_{AB}$=8.1Hz), 7.48(1H, d, J=8.1Hz), 7.91~7.94(1H, m), 8.15(1H, s), 8.48(1H, d, J=2.2Hz) |
| 53 | 4-sec.Bu | m.p.: 110.2~110.9° C. |

Then, preparation of intermediate compounds of the general formula (II) is described.

SYNTHESIS EXAMPLE 10

Intermediate No. 4

A mixture of 3.0 g of 1-diethoxymethyl-2-nitroiminoimidazolidine, 1.4 g of 4-fluoroaniline, and 1 ml of 3-dimethyl-2-imidazolidinone was agitated at 160° C. for 1 hour. About 20 ml of ethyl acetate was added to the reaction mixture. The resultant crystals were collected by filtration and the solvent was distilled off from the filtrate under reduced pressure to give 2.7 g of an oily residue, followed by purification with column chromatography [silica gel, eluent: hexane-ethyl acetate (1:2)] to obtain 0.87 g of 1-(4-fluorophenyliminomethyl)-2-nitroiminoimidazolidine.

SYNTHESIS EXAMPLE 11

Intermediate No. 12

A mixture of 2.0 g of of 1-diethoxymethyl-2-nitroiminoimidazolidine, 0.92 g of o-toluidine, 5 ml of THF and 0.12 g of a boron trifluoride ether complex was heated under reflux for 1 hour. The reaction mixture was poured into water, extracted with ethyl acetate, washed with water, dried and condensed. Ether was added to the resultant oily residue and the resultant crystals were separated by filtration and dried to give 1.2 g of 1-(2-methylphenyliminomethyl)-2-nitroiminoimidazolidine.

SYNTHESIS EXAMPLE 12

Intermediate No. 13

A mixture of 2.0 g of 1-diethoxymethyl-2-nitroiminoimidazolidine, 0.92 g of m-toluidine, 5 ml of dimethoxyethane and 0.12 g of a boron trifluoride ether complex was heated under reflux for 1 hour. The reaction mixture was poured into water, extracted with ethyl acetate, washed with water, dried and condensed. Ether was added to the resultant oily residue and the resultant crystals were separated by filtration and dried to give 1.1 g of 1-(3-methylphenyliminomethyl)-2-nitroiminoimidazolidine.

SYNTHESIS EXAMPLE 13

Intermediate No. 14

0.05 g of acetic acid was dropped in a mixture of 5.0 g of 1-diethoxymethyl-2-nitroiminoimidazolidine, 1.86 g of p-toluidine and 2 ml of 1,3-dimethyl-2-imidazolidinone at 120° C., followed by agitation at the same temperature for 3 hours. The reaction mixture was poured into water, extracted with ethyl acetate, washed with water, dried and condensed. Ether was added to the resultant oily residue and the resultant crystals were separated by filtration and dried to give 2.54 g of 1-(4-methylphenyliminomethyl)-2-nitroiminoimidazolidine.

SYNTHESIS EXAMPLE 14

Intermediate No. 18

0.05 g of trifluoroacetic acid was dropped in a mixture of 5.0 g of 1-diethoxymethyl-2-nitroiminoimidazolidine, 2.48 g of o-n-propylaniline and 2 ml of 1,3-dimethyl-2-imidazolidinone at 90° C., followed by agitation at the same temperature for 45 minutes. The reaction mixture was poured into water, extracted with ethyl acetate, washed with water, dried and evaporated. Ether was added to the resultant oily residue and the resultant crystals were separated by filtration and dried to give 1.6 g of 1-(2-n-propylphenyliminomethyl)-2-nitroiminoimidazolidine.

SYNTHESIS EXAMPLE 15

Intermediate No. 21

0.05 g of concentrated sulfuric acid was dropped in a mixture of 5.0 g of 1-diethoxymethyl-2-nitroiminoimidazolidine, 2.48 g of p-isopropylaniline and 2 ml of 1,3-dimethyl-2-imidazolidinone at 110° C., followed by agitation at the same temperature for 1 hour. The reaction mixture was poured into water, extracted with ethyl acetate, washed with water, dried and evaporated. Ether was added to the resultant oily residue and the resultant crystals were separated by filtration and dried to obtain 2.1 g of 1-(4-isopropylphenyliminomethyl)-2-nitroiminoimidazolidine.

SYNTHESIS EXAMPLE 16

Intermediate No. 27

A mixture of 60.6 g of 3,4-dimethylaniline, 200 g of ethyl orthoformate and 0.05 g of sulfuric acid was placed in a reactor equipped with Dean's stark tube and agitated at 140° to 165° C. for about 1 hour. After concentration of the reaction solution under reduced pressure, 45 g of nitroiminoimidazolidine and 70 g of 1,3-dimethyl-2-imidazolidinone were added and agitated at 140° to 160° C. for 2 hours. The reaction mixture was poured into 200 ml of a saturated saline solution, to which 150 ml of ethyl acetate was added. The resultant crystals were collected by filtration, washed with ethyl acetate and dried to give 40.2 g of 1-(3,4-dimethylphenyliminomethyl)-2-nitroiminoimidazolidine.

SYNTHESIS EXAMPLE 17

Intermediate No. 39

A mixture of 5.0 g of p-aminoacetophenone. 6.6 g of ethyl orthoformate, 5 ml of 1,3-dimethyl-2-imidazolidinone and 0.03 g of concentrated sulfuric acid was placed in a reactor equipped with Dean's stark tube and agitated at 140° C. for about 10 minutes, followed by further addition of 5.8 g of nitroiminoimidazolidine and agitation at 160° C. for 1 hour. The reaction mixture was poured into 200 ml of a saturated saline solution, to which 150 ml of ethyl acetate was added. The resultant crystals were collected by filtration, and dried to give 5.4 g of 1-(4-methylcarbonyl-phenyliminomethyl)-2-nitroiminoimidazolidine.

SYNTHESIS EXAMPLE 18

Intermediate No. 40

A mixture of 5.0 g of p-N,N-dimethylaminoaniline, 6.5 g of ethyl or orthoformate, 5 ml of 1,3-dimethyl-2-imidazolidinone and 0.03 g of concentrated sulfuric acid was placed in a reactor equipped with Dean's stark tube and agitated at 150° C. for about 10 minutes, followed by further addition of 5.7 g of nitroimidazolidine and agitation at 160° C. for 1 hour. The reaction mixture was poured into 200 ml of a saturated saline solution, to which 150 ml of ethyl acetate was added. The resultant crystals were collected by filtration, and dried to give 2.7 g of 1-(4-N,N-dimethyl-phenyliminomethyl)-2-nitroiminoimidazolidine.

SYNTHESIS EXAMPLE 19

Intermediate No. 41

A mixture of 10.0 g of ethyl p-aminobenzoate, 10.8 g of ethyl orthoformate, 10 ml of 1,3-dimethyl-2-imidazolidinone and 0.05 g of boron trifluoride ether complex was placed in a reactor equipped with Dean's stark tube and agitated at 140° C. for about 5 minutes, followed by further addition of 7.9 g of nitroiminoimidazolidine and agitation at 180° C. for 1 hour. The reaction mixture was poured into 200 ml of a saturated saline solution, to which 150 ml of ethyl acetate was added. The resultant crystals were collected by filtration and dried to give 12.3 g of 1-(4-ethoxy-carbonylphenyliminomethyl)-2-nitroiminoimidazolidine.

SYNTHESIS EXAMPLE 20

Intermediate No. 42

0.05 g of boron trifluoride ether complex was added under ice-cooling conditions to a mixture of 5.0 g of 1-diethoxymethyl-2-nitroiminoimidazolidine, 3.47 g of o-aminobenzotrifluoride and 5 ml of 1,3-dimethyl-2-imidazolidinone. Immediately, the reaction mixture was poured into water, extracted with ethyl acetate, washed with water, dried and concentrated. Ether was added to the resultant oily residue and the resultant crystals were removed by filtration, followed by washing with hot ethyl acetate to give 3.43 g of 1-(2-trifluoromethylphenyliminomethyl)-2-nitroiminoimidazolidine.

SYNTHESIS EXAMPLE 21

Intermediate No. 50

0.05 g of SnCl$_4$ was added to a mixture of 2.0 g of 1-diethoxymethyl-2-nitroiminoimidazolidine, 1.02 g of o-aminobenzonitrile and 5 ml of 1,3-dimethyl-2-imidazolidinone, followed by agitation at room temperature for 10 minutes. Ether was added to the reaction mixture, and the resultant crystals were collected by filtration and dried to give 2.9 g of 1-(2-cyanophenyliminomethyl)-2-nitroimino-imidazolidine.

SYNTHESIS EXAMPLE 22

Intermediate No. 50

0.05 g of boron trifluoride ether complex was added to a mixture of 2.0 g of 1-diethoxymethyl-2-nitroiminoimidazolidine, 1.02 g of o-aminobenzonitrile and 5 ml of acetonitrile followed by agitation at room temperature for 5 minutes. Ether was added to the reaction mixture, and the resultant crystals were collected by filtration and dried to give 2.2 g of 1-(2-cyanophenyliminomethyl)-2-nitroiminoimidazolidine.

SYNTHESIS EXAMPLE 23

Intermediate No. 50

0.05 g of boron trifluoride ether complex was added to a mixture of 2.0 g of 1-diethoxymethyl-2-nitroiminoimidazolidine, 1.02 g of o-aminobenzonitrile and 5 ml of DMF, followed by agitation at room temperature for 15 minutes. Ether was added to the reaction mixture, and the resultant crystals were collected by filtration and dried to give 1.9 g of 1-(2-cyanophenyliminomethyl)-2-nitroiminoimidazolidine.

SYNTHESIS EXAMPLE 24

Intermediate No. 51

0.05 g of boron trifluoride ether complex was added to a mixture of 46.4 g of 1-diethoxymethyl-2-nitroiminoimidazolidine, 27.8 g of 2-mercaptoaniline and 120 ml of 1,3-dimethyl-2-imidazolidinone under ice-cooling conditions, followed by agitation for 20 minutes. About 200 ml of ethyl acetate was added to the reaction mixture, and the resultant crystals were collected by filtration, washed with hexane and dried to give 61 g of 1-(2-methylmercaptophenyliminomethyl)-2-nitroiminoimidazolidine.

SYNTHESIS EXAMPLE 25

Intermediate No. 52

0.25 g of pyridine hydrochloride was added to a mixture of 5.0 g of 1-diethoxymethyl-2-nitroiminoimidazolidine, 3.64 g of o-aminobiphenyl and 3 ml of 1,3-dimethyl-2-imidazolidinone at 100° C., followed by agitation at the same temperature for 20 minutes. The reaction mixture was poured into water, extracted with ethyl ether, washed with water, dried and concentrated, followed by addition of ether to the resultant oily residue. The resulting crystals were collected by filtration and dried to give 3.2 g of 1-(2-phenylphenyliminomethyl)-2-nitroiminoimidazolidine.

Typical compounds of the formula (II) which could be obtained in the same manner as in Synthesis Examples 10 to 25 are shown in Table 2.

TABLE 2

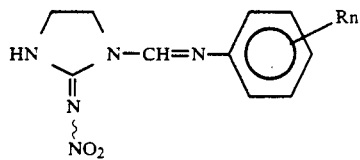

| Intermediate No. | $R_n$ | Values of Physical Properties |
|---|---|---|
| 1 | H | $\nu_{MAX}$(KBr)(cm$^{-1}$): 3311, 1639, 1591<br>$\delta_{TMS}$(CDCl$_3$)(ppm): 3.91~4.21(4H, m), 7.00~7.53(5H, m), 8.51(1H, s), 6.65(1H, broad-s)<br>m.p.: 173.0~179.0° C. |
| 2 | 2-F | $\delta_{TMS}$(CDCl$_3$)(ppm): 3.95~4.06(2H, m), 4.15~4.38(2H, m), 7.00~7.16(4H, m), 8.57(1H, s), 8.70(1H, broad-s) |
| 3 | 3-F | $\delta_{TMS}$(acetone-d$_6$)(ppm): 3.99~4.18(4H, m), 6.85~6.95(3H, m), 7.34~7.40(1H, m), 8.57(1H, s), 8.70(1H, broad-s) |
| 4 | 4-F | $\nu_{MAX}$(KBr)(cm$^{-1}$): 1646, 1595<br>$\delta_{TMS}$(CDCl$_3$)(ppm): 3.89~3.94(2H, m), 4.08~4.13(2H, m), 6.91~7.00(4H, m), 8.43(1H, s), 8.57(1H, broad-s)<br>m.p.: 145.0~148.9° C. |
| 5 | 2,6-F$_2$ | $\nu_{MAX}$(KBr)(cm$^{-1}$): 3419, 1637, 1615, 1509, 1466, 1281, 1239, 1003, 794<br>$\delta_{TMS}$(DMSO-d$_6$)(ppm): 3.89~3.95(2H, m), 4.07~4.12(2H, m), 7.07~7.18(3H, m), 8.57(1H, s), 9.98(1H, broad-s)<br>m.p.: 188.0~197.0° C. |
| 6 | 2-Cl | $\nu_{MAX}$(KBr)(cm$^{-1}$): 3365, 1630, 1592<br>$\delta_{TMS}$(CDCl$_3$)(ppm): 3.98~4.27(4H, m), 6.95~7.41(4H, m), 8.46(1H, s), 8.66(1H, broad-s)<br>m.p.: 171.0~174.0° C. |
| 7 | 3-Cl | $\delta_{TMS}$(acetone-d$_6$)(ppm): 4.00~4.07(2H, m), 4.10~4.18(2H, m), 7.05~7.19(3H, m), 7.31~7.37(1H, m), 8.45(1H, s), 9.36(1H, broad-s) |
| 8 | 4-Cl | $\nu_{MAX}$(KBr)(cm$^{-1}$): 3568, 1699, 1541<br>$\delta_{TMS}$(CDCl$_3$)(ppm): 3.97~4.20(4H, m), 7.00(2H, m), 7.29(2H, m), 8.51(1H, s), 8.64(1H, broad-s)<br>m.p.: 145.0~149.0° C. |
| 9 | 2-Br | $\nu_{MAX}$(KBr)(cm$^{-1}$): 3425, 1667, 1615, 1563<br>$\delta_{TMS}$(CDCl$_3$)(ppm): 3.90~3.97(2H, m), 4.15~4.19(2H, m), 6.96~7.07(2H, m), 7.26~7.30(1H, m), 7.55~7.57(1H, m), 8.40(1H, s), 9.68(1H, broad-s) |
| 10 | 3-Br | $\nu_{MAX}$(KBr)(cm$^{-1}$): 3364, 1636, 1587<br>$\delta_{TMS}$(CDCl$_3$)(ppm): 3.90~3.95(2H, m), 4.08~4.12(2H, m), 6.95(1H, d, J=8.8Hz), 7.36~7.43(2H, m), 8.13(1H, s), 8.46(1H, s), 9.71(1H, broad-s) |
| 11 | 4-Br | $\nu_{MAX}$(KBr)(cm$^{-1}$): 3377, 1644, 1587<br>$\delta_{TMS}$(CDCl$_3$)(ppm): 3.97~4.02(2H, m), 4.15~4.19(2H, m), 6.90~7.31(4H, m), 8.50(1H, s), 8.68(1H, broad-s)<br>m.p.: 128.0~137.0° C. |
| 12 | 2-CH$_3$ | $\nu_{MAX}$(KBr)(cm$^{-1}$): 3420, 1593<br>$\delta_{TMS}$(CDCl$_3$)(ppm): 2.26(3H, s), 3.94~4.21(4H, m), 6.84~7.23(4H, m), 8.42(1H, s), 8.69(1H, broad-s)<br>m.p.: 128.0~133.0° C. |
| 13 | 3-CH$_3$ | $\nu_{MAX}$(KBr)(cm$^{-1}$): 3423, 3204, 1685, 1596<br>$\delta_{TMS}$(CDCl$_3$)(ppm): 2.27(3H, s), 3.40~3.58(4H, m), 6.69~7.48(4H, m), 8.18(1H, s), 8.28(1H, broad-s)<br>m.p.: 143.0~147.0° C. |

TABLE 2-continued

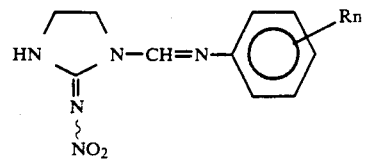

| Intermediate No. | $R_n$ | Values of Physical Properties |
|---|---|---|
| 14 | 4-CH$_3$ | $\nu_{MAX}$(KBr)(cm$^{-1}$): 3366, 1684, 1541<br>$\delta_{TMS}$(CDCl$_3$)(ppm): 2.34(3H, s), 3.95~3.98(2H, m), 4.16~4.21(2H, m), 6.98(2H, d, J$_{AB}$=8.8Hz), 7.13(2H, d, J$_{AB}$=8.8Hz), 8.52(1H, s), 8.62(1H, broad-s)<br>m.p.: 151.5~156.0° C. |
| 15 | 2-Et | $\delta_{TMS}$(CDCl$_3$)(ppm): 1.16(3H, t, J=7.3Hz), 2.67(2H, q, J=7.3Hz), 3.96~4.01(2H, m), 4.19~4.22(2H, m), 6.85~6.87(1H, m), 7.11~7.19(3H, m), 8.46(1H, s), 8.62(1H, broad-s)<br>m.p.: 115.5~119.5° C. |
| 16 | 3-Et | $\delta_{TMS}$(CDCl$_3$)(ppm): 1.22(3H, t, J=7.3Hz), 2.65(2H, q, J=7.3Hz), 4.00~4.06(2H, m), 4.14~4.18(2H, m), 6.90~7.19(3H, m), 7.23~7.26(1H, m), 8.44(1H, s), 9.32(1H, broad-s) |
| 17 | 4-Et | $\delta_{TMS}$(acetone-d$_6$)(ppm): 1.25(3H, t, J=7.3Hz), 2.62(2H, q, J=7.3Hz), 4.01~4.08(2H, m), 4.13~4.20(2H, m), 7.03(2H, d, J=8.8Hz), 7.19(2H, d, J=8.8Hz), 8.44(1H, s), 9.30(1H, broad-s) |
| 18 | 2-nPr | $\delta_{TMS}$(CDCl$_3$)(ppm): 0.92(3H, t, J=7.3Hz), 1.39~1.61(2H, m), 2.63(2H, t, J=7.3Hz), 3.96~4.01(2H, m), 4.04~4.22(2H, m), 6.87(1H, d, J=7.3Hz), 7.00~7.18(3H, m), 8.46(1H, s), 8.61(1H, broad-s) |
| 19 | 4-nPr | $\delta_{TMS}$(CDCl$_3$)(ppm): 0.93(3H, t, J=7.3Hz), 1.63(2H, tq, J=7.3Hz), 2.57(2H, t, J=7.3Hz), 3.95~4.00(2H, m), 4.17~4.22(2H, m), 6.99(1H, d, J$_{AB}$=8.1Hz), 7.13(1H, d, J$_{AB}$=8.1Hz), 8.53(1H, s), 8.61(1H, broad-s) |
| 20 | 2-iPr | $\delta_{TMS}$(CDCl$_3$)(ppm): 1.19(6H, d, J=6.6Hz), 3.30~3.41(1H, m), 3.97~4.01(2H, m), 4.19~4.24(2H, m), 6.82~6.85(1H, m), 7.12~7.18(3H, m), 7.25~7.27(1H, m), 8.46(1H, s), 8.62(1H, broad-s)<br>m.p.: 147.0~150.0° C. |
| 21 | 4-iPr | $\delta_{TMS}$(CDCl$_3$)(ppm): 1.24(6H, d, J=7.4Hz), 2.76~2.97(1H, m), 3.88~3.99(2H, m), 4.16~4.20(2H, m), 7.01(2H, d, J$_{AB}$=8.1Hz), 7.18(2H, d, J$_{AB}$=8.1Hz), 8.52(1H, s), 8.68(1H, broad-s) |
| 22 | 4-tBu | $\nu_{MAX}$(KBr)(cm$^{-1}$): 2960, 1678, 1582<br>$\delta_{TMS}$(CDCl$_3$)(ppm): 1.32(9H, s), 3.79~3.97(2H, m), 4.12~4.19(2H, m), 7.02(2H, d, J$_{AB}$=8.1Hz), 7.34(2H, d, J$_{AB}$=8.1Hz), 8.53(1H, s)<br>m.p.: 187.0~190.0° C. |
| 23 | 2,3-(CH$_3$)$_2$ | $\nu_{MAX}$(KBr)(cm$^{-1}$): 3249, 1654, 1522, 1474, 1270, 1049, 779<br>$\delta_{TMS}$(CDCl$_3$)(ppm): 2.19(3H, s), 2.26(3H, s), 4.03~4.07(2H, m), 4.18~4.22(2H, m), 6.76(1H, d, J=7.3Hz), 6.95(1H, d, J=7.3Hz), 7.04(1H, dd, J=7.3Hz), 8.31(1H, s), 9.30(1H, broad-s) |
| 24 | 2,4-(CH$_3$)$_2$ | $\nu_{MAX}$(KBr)(cm$^{-1}$): 3366, 1637, 1594, 1522, 1443, 1214, 1049, 833 |

TABLE 2-continued

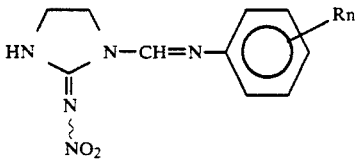

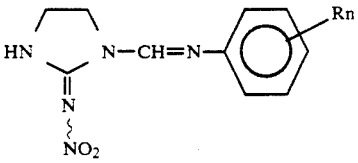

| Intermediate No. | $R_n$ | Values of Physical Properties |
|---|---|---|
| | | $\delta_{TMS}$(acetone-$d_6$)(ppm): 2.22(3H, s), 2.26(3H, s), 4.01~4.09(2H, m), 4.15~4.20(2H, m), 6.83(1H, d, J=7.3Hz), 6.97(1H, d, J=7.3Hz), 7.00(1H, s), 8.34(1H, s), 9.27(1H, broad-s) m.p.: 168.0~173.0° C. |
| 25 | 2,5-$(CH_3)_2$ | $\delta_{TMS}$($CDCl_3$)(ppm): 2.21(3H, s), 2.30(3H, s), 3.96~4.00(2H, m), 4.18~4.23(2H, m), 6.69(1H, s), 6.89(1H, d, J=7.3Hz), 7.05(1H, d, J=7.3Hz), 8.44(1H, s), 8.59(1H, broad-s) |
| 26 | 2,6-$(CH_3)_2$ | $\delta_{TMS}$($CDCl_3$)(ppm): 2.04(3H, s), 2.11(3H, s), 3.99~4.03(2H, m), 4.19~4.28(2H, m), 6.91(1H, t, J=8.1Hz), 7.01(2H, d, J=8.1Hz), 8.25(1H, s), 8.42(1H, broad-s) |
| 27 | 3,4-$(CH_3)_2$ | $\delta_{TMS}$($CDCl_3$)(ppm): 2.24(3H, s), 2.26(3H, s), 3.94~3.99(2H, m), 4.16~4.21(2H, m), 6.83(1H, dd, J=8.1Hz, J=2.2Hz), 6.88(1H, s), 7.08(1H, d, J=8.1Hz), 8.47(1H, s), 8.53(1H, s) m.p.: 196.0° C. (dec.) |
| 28 | 3,5-$(CH_3)_2$ | $\delta_{TMS}$($CDCl_3$)(ppm): 2.34(6H, s), 3.81~4.00(2H, m), 4.16~4.20(2H, m), 6.87(2H, s), 6.91(1H, s), 8.33(1H, s), 8.56(1H, s) |
| 29 | 2-$OCH_3$ | $\nu_{MAX}$(KBr)($cm^{-1}$): 3523, 3258, 1635, 1615 $\delta_{TMS}$($CDCl_3$)(ppm): 3.76(3H, s), 3.78~4.03(4H, m), 6.87~7.11(4H, m), 8.35(1H, s), 9.85(1H, broad-s) m.p.: 129.0~132.5° C. |
| 30 | 3-$OCH_3$ | $\nu_{MAX}$(KBr)($cm^{-1}$): 3411, 1685, 1605 $\delta_{TMS}$($CDCl_3$)(ppm): 3.79(3H, s), 4.01~4.09(2H, m), 4.13~4.17(2H, m), 6.66~6.82(2H, m), 7.13~7.26(2H, m), 8.43(1H, s), 9.31(1H, broad-s) m.p.: 128.0~132.0° C. |
| 31 | 4-$OCH_3$ | $\nu_{MAX}$(KBr)($cm^{-1}$): 3366, 1640, 1585 $\delta_{TMS}$($CDCl_3$)(ppm): 3.33(3H, s), 3.79~3.82(2H, m), 3.95~3.98(2H, m), 6.90(2H, d, $J_{AB}$=8.8Hz), 7.05(2H, d, $J_{AB}$=8.8Hz), 8.33(1H, s), 8.47(1H, broad-s) m.p.: 158.0~162.5° C. |
| 32 | 2-OEt | $\nu_{MAX}$(KBr)($cm^{-1}$): 3423, 3209, 1685, 1616 $\delta_{TMS}$($CDCl_3$)(ppm): 1.43(3H, t, J=7.0Hz), 3.81~4.00(2H, m), 4.06(2H, q, J=7.0Hz), 4.21~4.26(2H, m), 6.87~6.96(3H, m), 7.08~7.12(1H, m), 8.64(1H, s), 9.64(1H, broad-s) m.p.: 157.0~159.0° C. |
| 33 | 4-OEt | $\nu_{MAX}$(KBr)($cm^{-1}$): 3336, 2977, 1630, 1584 $\delta_{TMS}$($CDCl_3$)(ppm): 1.41(3H, t,), J=7.0Hz), 3.94~4.04(4H, m), 4.16~4.20(2H, m), 6.84(2H, d, $J_{AB}$=8.8Hz), 7.03(2H, d, $J_{AB}$=8.8Hz), 8.52(1H, s), 8.66(1H, broad-s) m.p.: 157.0~159.5° C. |
| 34 | 2-OiPr | $\delta_{TMS}$($CDCl_3$)(ppm): 1.33(6H, d, J=6.6Hz), 3.95~3.99(2H, m), 4.13~4.24(2H, m), 4.46~4.55(1H, m), 6.89~7.01(3H, m), 7.07~7.11(1H, m), 8.65(1H, s), 8.34(1H, broad-s) |
| 35 | 3-OiPr | $\delta_{TMS}$(acetone-$d_6$)(ppm): 1.30(6H, d, J=5.7Hz), 4.00~4.06(2H, m), 4.13~4.17(2H, m), 4.60~4.66(1H, m), 6.57~7.24(5H, m), 8.43(1H, s) |
| 36 | 4-OiPr | $\nu_{MAX}$(KBr)($cm^{-1}$): 3324, 1631, 1586, 1529, 1428, 1292, 1239, 830 $\delta_{TMS}$(acetone-$d_6$)(ppm): 1.29(6H, d, J=5.9Hz), 4.00~4.05(2H, m), 4.12~4.16(2H, m), 4.55~4.61(1H, m), 6.89(2H, d, $J_{AB}$=8.8Hz), 7.07(2H, d, $J_{AB}$=8.8Hz), 8.44(1H, s), 9.30(1H, broad-s) |
| 37 | 3,4-$OCH_2O$— | $\nu_{MAX}$(KBr)($cm^{-1}$): 3392, 1638, 1600, 1528, 1450, 1302, 1241, 1033, 927 $\delta_{TMS}$($CDCl_3$)(ppm): 3.81~3.92(2H, m), 3.99~4.06(2H, m), 5.97(2H, s), 6.51(1H, dd, J=8.1Hz, J=2.2Hz), 6.63(1H, d, J=2.2Hz), 6.76(1H, d, J=8.1Hz), 8.38(1H, s), 9.81(1H, broad-s) |
| 38 | 2-$COCH_3$ | $\delta_{TMS}$(DMSO-$d_6$)(ppm): 2.55(3H, s), 3.81~3.85(2H, m), 4.02~4.06(2H, m), 7.06~7.08(1H, m), 7.21~7.25(1H, m), 7.49~7.53(1H, m), 7.56~7.58(1H, m), 8.29(1H, s), 9.97(1H, broad-s) m.p.: 126.0~130.0° C. |
| 39 | 4-$COCH_3$ | $\nu_{MAX}$(KBr)($cm^{-1}$): 3336, 1673, 1645, 1594 $\delta_{TMS}$(acetone-$d_6$)(ppm): 2.56(3H, s), 4.01~4.09(2H, m), 4.17~4.22(2H, m), 7.21(2H, d, $J_{AB}$=8.1Hz), 7.99(2H, d, $J_{AB}$=8.1Hz), 8.49(1H, s), 9.40(1H, broad-s) m.p.: 165.0~168.0° C. |
| 40 | 4-$N(CH_3)_2$ | $\delta_{TMS}$($CDCl_3$)(ppm): 2.94(6H, s), 3.83~3.88(2H, m), 4.08~4.14(2H, m), 6.67(2H, d, $J_{AB}$=8.8Hz), 7.04(2H, d, $J_{AB}$=8.8Hz), 8.46(1H, broad-s), 8.51(1H, s) |
| 41 | 4-COOEt | $\nu_{MAX}$(KBr)($cm^{-1}$): 3329, 1710, 1644, 1598 $\delta_{TMS}$(DMSO-$d_6$)(ppm): 1.29~1.35(3H, m), 3.75~3.85(2H, m), 3.99~4.06(2H, m), 4.26~4.32(2H, m), 7.18(2H, d, $J_{AB}$=8.1Hz), 7.93(2H, d, $J_{AB}$=8.1Hz), 8.38(1H, s), 9.98(1H, broad-s) m.p.: 175.2~179.8° C. |
| 42 | 4-$CF_3$ | $\nu_{MAX}$(KBr)($cm^{-1}$): 1640, 1589, 1526 $\delta_{TMS}$(DMSO-$d_6$)(ppm): 3.81~3.86(2H, m), 3.97~4.01(2H, m), 7.22(1H, d, J=8.1Hz), 7.23~7.33(1H, m), 7.61~7.64(1H, m), 7.67(1H, d, J=8.1Hz), 8.34(1H, s), 9,99(1H, broad-s) m.p.: 174.8~175.3° C. (dec.) |
| 43 | 3-$CF_3$ | $\delta_{TMS}$($CDCl_3$)(ppm): 3.99~4.04(2H, m), 4.18~4.23(2H, m), 7.22~7.47(4H, m), 8.55(1H, s), 8.66(1H, broad-s) |
| 44 | 4-$CF_3$ | $\delta_{TMS}$($CDCl_3$)(ppm): 3.98~4.03(2H, m), 4.18~4.22(2H, m), 7.14(2H, d, J=8.1Hz), 7.59(2H, d, J=8.1Hz), 8.54(1H, s), 8.66(1H, broad-s) |
| 45 | 2-$OCF_3$ | $\nu_{MAX}$(KBr)($cm^{-1}$): 3332, 1644, 1530 $\delta_{TMS}$($CDCl_3$)(ppm): 3.92~4.03(2H, |

TABLE 2-continued

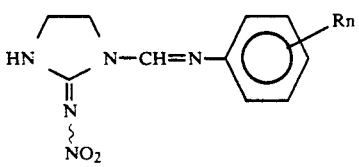

| Intermediate No. | $R_n$ | Values of Physical Properties |
|---|---|---|
| | | m), 4.19~4.24(2H, m), 7.03~7.06(1H, m), 7.18~7.20(1H, m), 7.25~7.28(2H, m), 8.51(1H, s), 8.67(1H, broad-s) |
| 46 | 4-OCF$_3$ | $\nu_{MAX}$(KBr)(cm$^{-1}$): 1634, 1607, 1526 $\delta_{TMS}$(DMSO-d$_6$)(ppm): 3.79~3.83(2H, m), 3.97~4.01(2H, m), 7.19(2H, d, J$_{AB}$=8.8Hz), 7.31(2H, d, J$_{AB}$=8.8Hz), 8.36(1H, s), 9.94(1H, broad-s) m.p.: 175.9~177.3° C. (dec.) |
| 47 | 3-OCHF$_2$ | $\nu_{MAX}$(KBr)(cm$^{-1}$): 3387, 1637, 1593 $\delta_{TMS}$(CDCl$_3$)(ppm): 3.97~4.02(2H, m), 4.16~4.20(2H, m), 6.52(1H, t, J=74.1Hz), 6.83(1H, d, j=2.2Hz), 6.90(1H, dd, J=8.1Hz, J=2.2Hz), 6.93(1H, dd, J=8.1Hz, J=2.2Hz), 7.31(1H, t, J=8.1Hz), 8.51(1H, s), 8.71(1H, broad-s) |
| 48 | 2-NO$_2$ | $\nu_{MAX}$(neat)(cm$^{-1}$): 1687, 1644 $\delta_{TMS}$(DMSO-d$_6$)(ppm): 3.80~3.84(2H, m), 3.92~3.94(2H, m), 7.27(1H, d, J=8.1Hz), 7.31~7.34(1H, m), 7.61~7.65(1H, m), 7.84~7.88(1H, m), 8.40(1H, s), 10.04(1H, broad-s) |
| 49 | 3-NO$_2$ | $\nu_{MAX}$(neat)(cm$^{-1}$): 1683, 1614, 1563, 1524 $\delta_{TMS}$(DMSO-d$_6$)(ppm): 3.80~3.84(2H, m), 3.92~3.94(2H, m), 7.27(1H, d, J=8.1Hz), 7.31~7.34(1H, m), 7.61~7.65(1H, m), 7.84~7.88(1H, m), 8.40(1H, s), 10.04(1H, broad-s) |
| 50 | 2-CN | $\nu_{MAX}$(KBr)(cm$^{-1}$): 3342, 2229, 1636, 1523 $\delta_{TMS}$(DMSO-d$_6$)(ppm): 3.83~3.87(2H, m), 4.01~4.05(2H, m), 7.28~7.34(2H, m), 7.63~7.67(1H, m), 7.77(1H, d, J=7.3Hz), 8.47(1H, s), 10.05(1H, broad-s) |
| 51 | 2-SCH$_3$ | $\nu_{MAX}$(KBr)(cm$^{-1}$): 1643, 1597, 1552 $\delta_{TMS}$(DMSO-d$_6$)(ppm): 2.37(3H, s), 3.81~3.86(2H, m), 3.99~4.04(2H, m), 6.96(1H, d, J=7.3Hz), 7.08~7.17(3H, m), 8.29(1H, s), 9.92(1H, broad-s) m.p.: 204.8~206.9° C. (dec.) |
| 52 | 2-Ph | $\delta_{TMS}$(CDCl$_3$)(ppm): 3.85~3.89(2H, m), 3.96~4.01(2H, m), 6.97~7.44(9H, m), 8.00(1H, broad-s), 8.46(1H, s) |
| 53 | 4-OPh | $\delta_{TMS}$(CDCl$_3$)(ppm): 3.95~3.99(2H, m), 4.16~4.21(2H, m), 6.97~7.35(9H, m), 8.11(1H, broad-s), 8.53(1H, s) |
| 54 | 2-CH$_2$Ph | $\nu_{MAX}$(KBr)(cm$^{-1}$): 3333, 1632, 1588 $\delta_{TMS}$(CDCl$_3$)(ppm): 3.89~3.99(2H, m), 4.04(2H, s), 4.07~4.12(2H, m), 6.92(1H, d, J=8.1Hz), 7.05~7.29(8H, m), 7.68(1H, broad-s), 8.39(1H, s) |
| 55 | 3-OH | $\delta_{TMS}$(DMSO-d$_6$)(ppm): 3.75~3.82(2H, m), 3.95~4.04(2H, m), 6.45~6.50(2H, m), 6.55~6.59(1H, m), 7.08~7.16(1H, m), 8.30(1H, s), 9.42(1H, broad-s), 9.88(1H, broad-s) |
| 56 | 4-OH | $\delta_{TMS}$(DMSO-d$_6$)(ppm): 3.76~3.81(2H, m), 3.94~3.98(2H, m), 6.72(2H, d, J$_{AB}$=8.8Hz), 6.94(2H, |

TABLE 2-continued

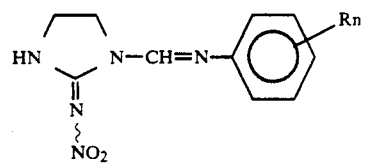

| Intermediate No. | $R_n$ | Values of Physical Properties |
|---|---|---|
| | | d, J$_{AB}$=8.8Hz), 8.31(1H, s), 9.28(1H, broad-s), 9.81(1H, broad-s) |

The process for preparing intermediates of the general formula (V) is described.

SYNTHESIS EXAMPLE 26

A mixture of 25 of 2-nitroiminoimidazolidine, 100 g of ethyl o-formats and 25 ml of 1,3-dimethyl-2-imidazoldinone was heated under reflux for 3 hours. After cooling to room temperature, the reaction solution was poured into water and extracted with ethyl acetate. After washing with water and drying (anhydrous magnesium sulfate), the solvent was evaporated under reduced pressure. The resultant crystals were sludged with ether to give 32 g of 1-diethoxymethyl-2-nitroiminoimidazolidine.

m.p.: 100.2° to 101.8° C.

$\nu_{MAX}$ (KBr) (cm$^{-1}$): 3340, 1570, 1530, 1470, 1440, 1280, 1220, 1170, 1090, 1040, 1010

$\delta_{TMS}$ (CDCl$_3$) (ppm): 1.24(6H,t, J=6.9Hz), 3.44~3.87 (8H,m), 5.95(1H,s), 8.36(1H,s)

Elementary analysis (for $C_8H_{16}N_4O_4$)

| | C | H | N |
|---|---|---|---|
| calculated (%) | 41.37 | 6.94 | 24.13 |
| found (%) | 40.94 | 6.90 | 24.58 |

The compositions of the invention are more particularly described by way of Preparation Examples.

FORMULATION EXAMPLE 1

20 parts by weight of each of compounds of the invention, 10 parts by weight of Sorpol 355S (surfactant available from Toho Chem. Co., Ltd.) and 70 parts by weight of xylene were uniformly agitated and mixed to obtain an emulsion.

FORMULATION EXAMPLE 2

20 parts by weight of each of compounds of the invention, 2 parts by weight of sodium alkylnaphthalenesulfonate, 5 parts by weight of sodium ligninsulfonate, 5 parts by weight of white carbon and 68 parts by weight of diatomaceous earth were uniformly agitated and mixed to obtain a wettable powder.

FORMULATION EXAMPLE 3

0.3 parts by weight of each of compounds of the invention was dissolved in acetone. While mixing with 99.7 parts by weight of clay, the acetone was evaporated to obtain a powder.

FORMULATION EXAMPLE 4

2 parts by weight of each of compounds of the invention, 2 parts by weight of sodium ligninsulfonate, and 96 parts by weight of bentonite were uniformly divided into pieces and mixed, to which water was added for kneading, followed by granulation and drying to obtain a granular.

FORMULATION EXAMPLE 5

98 parts by weight of a mixture of clay and talc (mixing ratio of 7:3) and 2 parts by weight of Cellogen (commercial name of Daiichi Ind. Pharm. Co., Ltd.) were broken into pieces and mixed, to which water was added. The mixture was granulated and dried to obtain granules. 20 parts by weight of an acetone solution of 10% of each of compounds of the invention was added to 98 parts by weight of the granules, followed by evaporating the acetone to obtain a granular.

The insecticidal activity of the compounds of the formula (I) is particularly described by way of test examples.

TEST EXAMPLE 1

Effect on *Laodelphax striatellus* Fallen—Small brown planthopper

The emulsion prepared in Formulation Example 1 was diluted to predetermined concentrations and 2 ml of each diluted emulsion was applied over a bundle of several rice seedlings (about third lead stage). After drying in air, the treated seedlings were covered with a metal gauze cylinder, in which ten female adult worms of the smaller brown planthopper were released, followed by placing in a temperature controlled chamber at 25° C. After 48 hours, the mortality was checked. The results are shown in Tables 3 and 4. For a control chemical, there was used BPMC (0-8-sec-butyl)phenyl N-methylcarbamate).

TABLE 3

| Effect on Small Brown Planthopper | |
|---|---|
| Tested Compound | Mortality (%) 100 ppm |
| Compound Nos. 1~53 | 100 |
| BPMC | 30 |

TABLE 4

| Effect on Small Brown Planthopper | |
|---|---|
| Tested Compound | Mortality (%) 10 ppm |
| Compound Nos. 4, 9~16, 18~20, 23, 24, 28, 30~36, 39, 42, 47, 49 | 100 |
| BPMC | 0 |

TEST EXAMPLE 2

Effect on resistant *Nephotettix cincticepts* Uhler—Resistant green rice leafhopper The emulsions prepared in Formulation Example 1 were each diluted to predetermined concentrations and each solution was applied in an amount of 3 ml over a bundle of several rice seedlings (about third lead stage). After drying in air, the treated seedlings were covered with a metal gauze cylinder, in which an organophosphate agent and ten carbamate-resistant female adult worms of the rice leafhopper were placed, followed by placing in a temperature controlled chamber at 25° C. After 48 hours, the mortality was checked. The results are shown in Tables 5 and 6. For a control chemical, there was used as diazinon, [O,O-diethyl-O-(2-isopropyl-6-methyl-4-pyrimidinyl)phosphorothioate].

TABLE 5

| Effect on Resistant Green Rice Leafhopper | |
|---|---|
| Tested Compound | Mortality (%) 100 ppm |
| Compound Nos. 1~53 | 100 |
| Diadinon | 35 |

TABLE 6

| Effect on Resistant Green Rice Leafhopper | |
|---|---|
| Tested Compound | Mortality (%) 10 ppm |
| Compound Nos. 4, 9~16, 18~20, 23, 24, 28, 30~36, 39, 42, 47, 49 | 100 |
| Diadinon | 10 |

TEST EXAMPLE 3

Effect on *Callosobruchus chinesis* Linne—Azuki bean weevil

An acetone solution of each of the compounds of the invention was placed on a laboratory dish with a diameter of 9 cm, followed by removal of the acetone by evaporation. Twenty female adults worms of the Azuki bean weevil, which were 2 to 3 days after emergence were placed in the dish at 25° C. After 48 hours, the insect killing rate was checked. The results are shown in Table 7.

TABLE 7

| Effect on Azuki Bean Weevil | |
|---|---|
| Tested Compound | Mortality (%) 0.01 mg/dish |
| Compound Nos. 1~53 | 100 |
| Diadinon | 60 |

TEST EXAMPLE 4

Effect on *Myzus persicae* Sulzer green peach aphid

Dilutions of the emulsions prepared in Formulation Example 1 were each applied in an amount of 20 ml over potted eggplant seedlings (fourth or fifth leaf stage) which were grown in a greenhouse and on which the green peach aphid had been parasitic. After the application, the seedlings were placed in t he greenhouse and, after three days, the number of the aphids were checked. The results are shown in Table 8.

TABLE 8

| Effect on Green Peach Aphid | | |
|---|---|---|
| Tested Compound | Concentration | Viability |
| Compound Nos. 1~53 | 50 ppm | 0~5 |
| DDVP | 50 ppm | 66 |
| Not-treated | | 135 |

Viability = 100 × (number of aphids after application)/(number of aphids prior to application)

As will be apparent from the foregoing description, the imidazolidine derivatives of the formula (I) according to the invention have high insecticidal efficacy and a wide insecticidal spectrum. The imidazolidine derivatives of the formula (I) can be readily prepared according to a process of the invention using novel intermediates of the formula (II). The agricultural chemicals comprising the imidazolidine derivatives of the formula (I) have good characteristics as an insecticide.

What is claimed is:

1. An imidazolidine compound of the formula

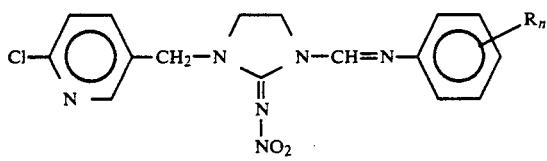

wherein each R represents a hydrogen atom, an alkyl group having from 1 to 6 carbon atoms, a halogen atom, an alkoxy group having from 1 to 6 carbon atoms, a methylenedioxy group, an alkylthio group having from 1 to 4 carbon atoms, a haloalkyl group having from 1 to 2 carbon atoms, a haloalkoxy group having from 1 to 4 carbon atoms, an alkylcarbonyl group having from 1 to 6 carbon atoms, an alkoxycarbonyl group having from 1 to 6 carbon atoms, a hydroxy group, a cyano group, a nitro group, an alkylamino group having from 1 to 8 carbon atoms, a phenyl group, a phenoxy group, a benzyl group or a halopyridylmethyloxy group, and n is an integer of from 1 to 3.

2. An imidazoline compound of claim 1, wherein each R is a hydrogen atom.

3. An imidazoline compound of claim 1, wherein each R is a halogen atom and n is 1 or 2.

4. An imidazoline compound of claim 1, wherein each R is a fluorine atom and n is 1 or 2.

5. An imidazoline compound of claim 1, wherein each R is alkyl of 1 to 6 carbon atoms and n is 1 or 2.

6. An imidazoline compound of claim 1, wherein n is 1 and R is alkoxy of 1 to 6 carbon atoms.

7. An imidazoline compound of claim 1, wherein n is 1 and R is methylenedioxy.

8. An imidazoline compound of claim 1, wherein n is 1 and R is alkylcarbonyl of 1 to 6 carbon atoms.

9. An imidazoline compound of claim 1, wherein n is 1 and R is trifluoromethyl.

10. An imidazoline compound of claim 1, wherein n is 1 and R is trifluoromethoxy.

11. An imidazoline compound of claim 1, wherein n is 1 and R is phenyl.

12. An imidazoline compound of claim 1, wherein n is 1 and R is phenoxy.

13. An imidazoline compound of claim 1, wherein n is 1 and R is alkylthio.

14. An imidazoline compound of claim 1, wherein n is 1 insecticidally effective amount of an imidazoline compound of claim 1.

* * * * *